US011116584B2

(12) United States Patent
Dekel et al.

(10) Patent No.: US 11,116,584 B2
(45) Date of Patent: Sep. 14, 2021

(54) ROBOTIC SURGICAL TOOL

(71) Applicant: CLARONAV INC., North York (CA)

(72) Inventors: Doron Dekel, Toronto (CA); Razvan Mitulescu, Markham (CA)

(73) Assignee: Claronav Inc., North York (CA)

( * ) Notice: Subject to any disclaimer, the term of this patent is extended or adjusted under 35 U.S.C. 154(b) by 345 days.

(21) Appl. No.: 16/252,866

(22) Filed: Jan. 21, 2019

(65) Prior Publication Data
US 2019/0223957 A1 Jul. 25, 2019

Related U.S. Application Data

(60) Provisional application No. 62/620,006, filed on Jan. 22, 2018.

(51) Int. Cl.
*A61B 34/20* (2016.01)
*A61C 1/08* (2006.01)
(Continued)

(52) U.S. Cl.
CPC .............. *A61B 34/20* (2016.02); *A61B 34/10* (2016.02); *A61B 90/39* (2016.02); *A61C 1/082* (2013.01);
(Continued)

(58) Field of Classification Search
CPC ... A61B 34/10; A61B 34/20; A61B 2034/107; A61B 2034/108; A61B 2034/2046;
(Continued)

(56) References Cited

U.S. PATENT DOCUMENTS 7,346,417 B2   3/2008  Lüth et al.
9,119,655 B2   9/2015  Bowling et al.
(Continued)

OTHER PUBLICATIONS

Yang et al., "Manipulator Design and Operation of a Six-Degree-of-Freedom Handheld Tremor-Canceling Microsurgical Instrument", IEEE/ASME Transactions on Mechatronics, vol. 20, No. 2, Apr. 2015.
(Continued)

*Primary Examiner* — Robert A Lynch
(74) *Attorney, Agent, or Firm* — Bereskin & Parr LLP/S.E.N.C.R.L., s.r.l.

(57) ABSTRACT

Surgical systems and methods of controlling a surgical instrument are provided. The system includes a surgical instrument having a cutting portion and a body, the body having a handle, a drive motor for driving the cutting portion in a rotating, a reciprocating or a vibrating motion, a plurality of adjustment motors for adjusting a cutting pose of the cutting portion relative to the handle; and, a controller configured to measure the deviations between the cutting pose and a desired pose of the cutting portion and to activate the adjustment motors to reduce those deviations. The method involves coupling a cutting portion of a surgical instrument to a plurality of adjustment motors; holding the handle of the surgical instrument; operating a controller to measure deviations between a cutting pose and a desired pose; and operating the adjustment motors to adjust the cutting pose relative to the handle to reduce the deviations.

21 Claims, 16 Drawing Sheets

(51) Int. Cl.
*A61B 34/10* (2016.01)
*A61B 90/00* (2016.01)
*A61C 9/00* (2006.01)
*A61B 34/30* (2016.01)

(52) U.S. Cl.
CPC .............. *A61C 1/084* (2013.01); *A61C 9/004* (2013.01); *A61B 34/30* (2016.02); *A61B 2034/107* (2016.02); *A61B 2034/2051* (2016.02); *A61B 2034/2055* (2016.02); *A61B 2034/2059* (2016.02); *A61B 2034/2065* (2016.02); *A61B 2090/3983* (2016.02)

(58) Field of Classification Search
CPC .... A61B 2034/2051; A61B 2034/2059; A61B 2034/2065; A61B 2090/3983; A61B 17/1624; A61B 17/1626; A61C 1/082; A61C 1/084
See application file for complete search history.

(56) References Cited

U.S. PATENT DOCUMENTS

| | | |
|---|---|---|
| 9,125,624 B2 | 9/2015 | Dekel et al. |
| 9,402,691 B2 | 8/2016 | Merritt et al. |
| 9,554,872 B2 | 1/2017 | Koubi et al. |
| 9,707,043 B2 | 7/2017 | Bozung |
| 2011/0130761 A1* | 6/2011 | Plaskos ................. A61B 34/30 606/87 |
| 2012/0143084 A1* | 6/2012 | Shoham ............. A61B 17/1675 600/567 |
| 2013/0060278 A1 | 3/2013 | Bozung et al. |
| 2015/0182285 A1* | 7/2015 | Yen ....................... A61B 34/76 606/80 |
| 2017/0258532 A1 | 9/2017 | Shalayev et al. |

OTHER PUBLICATIONS

International Search Report and Written Opinion dated Apr. 15, 2019 in respect of PCT/CA2019/050071.

\* cited by examiner

ROBOTIC SURGICAL TOOL

PRIORITY

This application claims the benefit of U.S. Provisional Patent Application No. 62/620,006, filed Jan. 22, 2018, which is incorporated herein by reference in its entirety.

FIELD

The described embodiments relate to the field of medicine, in particular, the field of surgical navigation systems.

INTRODUCTION

Surgical navigation systems are increasingly common and commercially available. Many existing navigation systems, such as the dental navigation system described in U.S. Pat. Nos. 9,125,624 and 9,402,691 involve a three-dimensional (3D) coordinate mapping between locations in a subject jaw, that is, the patient's jaw that is being optically tracked, and homologous locations in a pre-acquired volumetric computed tomography (CT) image of that subject jaw.

In such surgical navigation systems, a drilling or cutting plan is prepared by a user in reference to the volumetric CT image of the subject jaw. The plan includes desired drilling and/or cutting paths for the cutting end of a tooltip. The tooltip can be a drill, a saw, or other surgical tool. During surgery, as the tooltip is positioned near the planned path, the navigation system uses the 3D coordinate mapping to dynamically and graphically indicate the magnitude and direction of geometrical deviations between the actual position of the tooltip and the desired position of the tooltip as set out in the planned path. The graphical deviation indicators guide the user to correct the tooltip position and orientation to more closely match the plan. However, since the tooltip can be free to move in all directions and orientations, that is, the tooltip can have 6 degrees of freedom (DOF), it can be a challenge to achieve the planned path with a desired level of accuracy.

SUMMARY

The various embodiments described herein generally relate to surgical systems and methods of controlling a surgical instrument.

An example surgical system includes a surgical instrument having a cutting portion and a body, the body having a handle, a drive motor for driving the cutting portion in a rotating, a reciprocating or a vibrating motion, a plurality of adjustment motors for adjusting a cutting pose of the cutting portion relative to the handle in a plurality of degrees of freedom; and, a controller configured to measure the deviations between the cutting pose of the cutting portion and a desired pose of the cutting portion in the plurality of degrees of freedom and to then activate the adjustment motors to reduce those deviations.

In at least one embodiment, the plurality of adjustment motors can be connected to the cutting portion to, in operation, adjust the pose of the cutting portion to reduce the deviations while a force of 5 Newtons (N) is applied to the cutting portion in a direction opposing the adjustment.

In at least one embodiment, the controller can further include a pose tracking system for tracking a pose of the cutting portion of the instrument relative to the anatomical region being operated on; a computer-readable memory for storing a geometrical descriptor of a cutting path or region within the anatomical region; and a processor in electronic communication with the computer-readable memory and the pose tracking system, configured to determine the deviations based on the pose reported by the pose tracking system and the desired pose determined from the geometrical descriptor.

In at least one embodiment, the pose tracking system can further include a first marker attached to the anatomical region; an second marker attached to a part of the body of the surgical instrument; a sensor for measuring a value indicative of the spatial relationship between the cutting portion and the part of the body of the surgical instrument to which the second marker is attached; and a pose tracking system for measuring the spatial relationship between the first and second markers; and the processor can be configured to compute the cutting pose of the cutting portion relative to the anatomical region based on the measurements obtained from the pose tracking system and the sensor.

In at least one embodiment, the geometrical descriptor can include a linear drilling path; the cutting portion can include a drill bit rotatable around a drilling axis; the drive motor can drive the drill bit in the rotating motion about the drilling axis; and, the deviations can include two angles of difference in orientation between the drilling axis and the drilling path.

In at least one embodiment, the geometrical descriptor can include a linear drilling path; the cutting portion can include a drill bit rotating around a drilling axis; the drive motor can drive the drill bit in the rotating motion about the drilling axis; and, the deviations can include a 2-dimensional translation vector describing the difference between a location on the drilling axis and a location on the drilling path.

In at least one embodiment, the surgical instrument can further include a head, and a pivotable attachment attaching the head to the body, the head can include the cutting portion; the surgical instrument can further include a driveshaft for transmitting torque from the drive motor to the cutting portion within a contact region; the head can include a cutting portion contact surface located within the contact region, the cutting portion contact surface being coupled to the cutting portion to drive the cutting portion; the body can include a torque transmission surface located within the contact region, the torque transmission surface being coupled to the driveshaft to be driven by the driveshaft, the torque transmission surface contacting the cutting portion contact surface to transfer torque thereto; and the cutting portion contact surface and the torque transmission surface can remain in contact through a range of adjustments in the plurality of degrees of freedom to transmit torque from the drive motor to the cutting portion.

In at least one embodiment, the surgical instrument can further include a driveshaft for transmitting torque from the drive motor to the cutting portion; and the surgical instrument can further include a head comprising the cutting portion, and a pivotable attachment attaching the head to the handle such that the roll axis of the head relative to the handle is co-axial with the roll axis of the driveshaft.

In at least one embodiment, the plurality of adjustment motors can include a head translation motor configured to rotate the head relative to the handle around an axis substantially perpendicular to both the roll axis and a lateral adjustment direction.

In at least one embodiment, the distance from the cutting portion to the target marker attached to a part of the body of the surgical instrument can be at least 5 centimeters (cm).

In at least one embodiment, the geometrical descriptor can be defined relative to an image of the anatomical region; and the processor can be further configured to compute a registration mapping between the image and the anatomical region, and to use that registration mapping in determining the deviations.

In at least one embodiment, the system can further include a display indicating the deviations between an imaginary pose of the cutting portion when each adjustment motor is set to approximately a middle 20% of its operating range and the desired pose of the cutting portion.

In at least one embodiment, the cutting region can be a cutting path; and the cutting portion can be a saw.

In at least one embodiment, the cutting region can be a 3D volume to be removed from the anatomical region; and the cutting portion can be a burr.

In at least one embodiment, the adjustment motors can be detachable from the parts of the instrument comprising the handle and the cutting portion such that the handle and the cutting portion are steam sterilizable without sterilizing the adjustment motors when the adjustment motors are detached.

An example method of controlling a surgical instrument involves coupling a cutting portion of a surgical instrument to a plurality of adjustment motors; holding in a human hand, the handle of the surgical instrument; operating a computerized controller to measure deviations between a cutting pose of the cutting portion and a desired pose of the cutting portion; and then operating the plurality of adjustment motors to adjust the cutting pose relative to the handle in a plurality of degrees of freedom to reduce the deviations.

In at least one embodiment, the method can further involve storing in a computer-readable memory in electronic communication with the computerized controller, a geometrical descriptor of a cutting path or region within an anatomical region being operated on; and operating the computerized controller to determine the desired pose from the geometrical descriptor; wherein, the computerized controller includes a pose tracking system; and operating the computerized controller to measure deviations between the cutting pose and the desired pose of the cutting portion can involve tracking the cutting pose relative to the anatomical region.

In at least one embodiment, the method can further involve defining the geometrical descriptor relative to an image of the anatomical region; and, operating the computerized controller to measure deviations between the cutting pose and the desired pose of the cutting portion can involve operating the computerized controller to compute a registration mapping between the image and the anatomical region, and then using that registration mapping to determine the deviations.

In at least one embodiment, the method can further involve, after completing a use of the surgical instrument involving operating the plurality of adjustment motors to adjust the cutting pose relative to the handle, detaching the adjustment motors from the surgical instrument and the cutting portion thereof; sterilizing the surgical instrument without the adjustment motors but including the cutting portion; and then reattaching the adjustment motors to the surgical instrument and the cutting portion thereof.

BRIEF DESCRIPTION OF THE DRAWINGS

Several embodiments will now be described in detail with reference to the drawings, in which.

Figure 1:
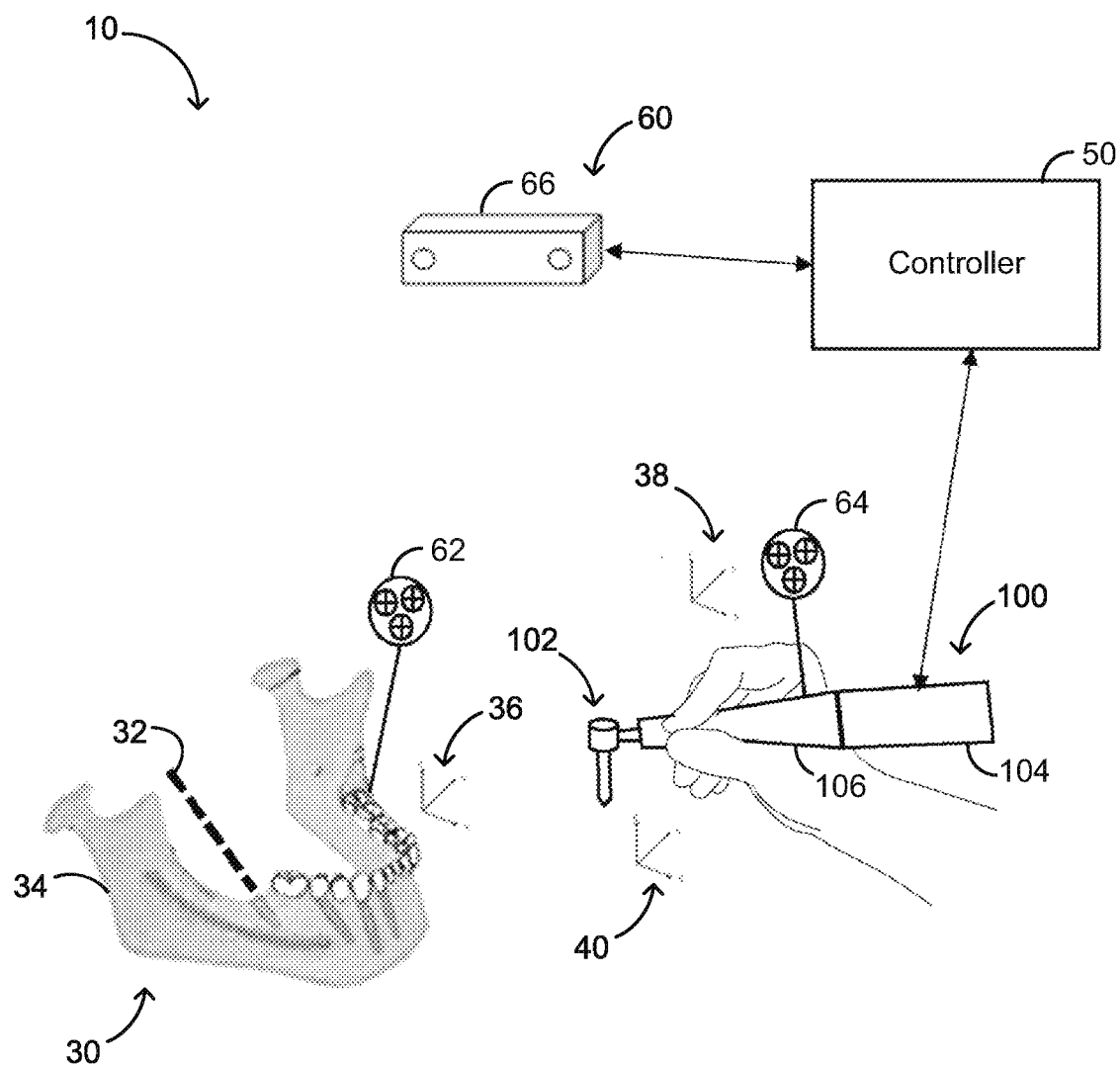
FIG. 1 is an example illustration of a surgical navigation system, according to at least one embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In some embodiments, aspects of methods described herein, such as method 400 described with reference to FIG. 16 below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication component. For example and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication component may be a network communication interface. In embodiments in which elements are combined, the communication component may be a software communication interface, such as those for inter-process communication (IPC). In still other embodiments, there may be a combination of communication components implemented as hardware, software, and combination thereof.

Program code may be applied to input data to perform the functions described herein and to generate output information. The output information is applied to one or more output devices, in known fashion. Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Referring now to FIG. 1, shown therein is an example illustration of a surgical navigation system 10, according to at least one embodiment. The surgical navigation system 10 includes a surgical instrument 100 and a controller 50. Also shown in FIG. 1 is a surgical subject 30, which may be an anatomical region of a patient, and a pose tracking system 60. In at least one embodiment, the surgical navigation system 10 can be used in dental surgery. In such embodiments, the surgical subject 30 can be a patient's jaw 34.

The surgical instrument 100 may also be referred to as handpiece 100. The surgical instrument 100 has a cutting portion 102 and a body 104. The body 104 includes a handle 106 that can be manually held and manipulated by a user. The surgical instrument 100 can also include at least one actuator (not shown in FIG. 1) to move the cutting portion 102 relative to the handle 106. In particular, the at least one actuator can drive the cutting portion 102 in at least one of a rotating, reciprocating, and vibrating motion or adjust a pose of the cutting portion 102 relative to the handle, that is adjust at least one of the tilt, roll, and translation of the cutting portion 102 relative to the handle 106. The cutting portion 102 includes a tooltip, the end of which can be used for cutting into a subject. For example, the tooltip can be a drill, or saw, or other tissue manipulation tool. For example, if a bone needs to be cut, the tooltip can be a saw.

The pose tracking system 60 may also be referred to as a motion tracking system 60. The pose tracking system 60 includes at least two target markers 62, 64 trackable by the pose tracking system 60. At least a first target marker 62 is rigidly attached to the surgical subject 30. At least a second target marker 64 is rigidly attached to the body 104 of the surgical instrument 100. Although only two target markers 62, 64 are shown in FIG. 1, in some embodiments, the pose tracking system 60 can include more target markers. Similarly, although only one pose tracking system 60 is shown in FIG. 1, the system 100 can include more pose tracking systems. Also, although pose tracking system 60 is illustrated in FIGS. 1, 3, 9, and 10 as an optical pose tracking system, other types of pose tracking systems 60 can be used. For example, electromagnetic, ultrasound, or inertial pose or motion tracking systems can be used. Furthermore, the choice of pose tracking system can depend on the type of surgery that it is used for.

The pose tracking system 60 can be configured for measuring changes to the pose of the at least two target markers 62, 64. Changes in the pose of the first target marker 62 attached to the surgical subject 30 is indicative of the changes in the pose of the surgical subject 30 within a subject coordinate space 36, such as changes to the pose of the patient's jaw 34. Similarly, changes in the pose of the second target marker 64 attached to part of the body 104 of the surgical instrument 100 is indicative of the changes in the pose of the part of the body 104 of the surgical instrument 100 within a handpiece coordinate space 38. For example, as shown in FIG. 1, the second target marker 64 can be attached to the handle 106 and changes in the pose of the second target marker 64 is indicative of changes in the pose of the handle 106 within the handpiece coordinate space 38. The pose tracking system 60 can measure the spatial relationship between the second target marker 64 attached to the part of the body 104 of the surgical instrument 100 and the first target marker 62 attached to the surgical subject 30.

In addition, the pose tracking system 60 can include a sensor to measure a value indicative of the spatial relationship between the cutting portion 102 and the part of the body 104 to which the second target marker 64 is attached. Thus, changes in the pose of the second target marker 64 attached to part of the body 104 of the surgical instrument 100 can be also indicative of the changes to the pose of the cutting portion 102 within a cutting portion coordinate space 40, namely a cutting pose of the cutting portion 102 of the surgical instrument 100. Furthermore, the pose tracking system 60 can measure the cutting pose of the cutting portion 102 of the surgical instrument 100 relative to the surgical subject 30.

It should be noted that the cutting portion 102 can be rigidly coupled to the second target marker 64 positioned remotely from it, to be detectable by the pose tracking system 60, even when the cutting portion 102 is hidden from the pose tracking system 60. For example, the distance from the cutting portion 102 to the second target marker 64 attached to a part of the body 104 of the surgical instrument 100 can be at least 5 centimeters (cm). When the cutting portion 102 is rigidly coupled to the second target marker, the pose tracking system 60 may not include a sensor to measure a value indicative of the spatial relationship between the cutting portion 102 and marker 64.

When the cutting portion 102 is rigidly attached to the body 104, the cutting portion coordinate space 40 has a fixed geometrical relationship with the handpiece coordinate space 38. Thus, once the mapping between the subject coordinate space 36 and the handpiece coordinate space 38 is measured and recorded, a model of the cutting portion 102 in the handpiece coordinate space 38 can be mapped to the subject coordinate space 36 using methods of existing surgical navigation systems.

However, as noted above, the cutting portion 102 can move relative to the handle 106 by the at least one actuator. Thus, to map a model of the cutting portion 102 in the handpiece coordinate space 38 to the subject coordinate space 36, a current state of the at least one actuator can be required in order to determine a current geometrical relationship between the cutting portion coordinate space 40 and the handpiece coordinate space 38. Once the mapping between the subject coordinate space 36 and the handpiece coordinate space 38 is measured and recorded and the current geometrical relationship between the cutting portion coordinate space 40 and the handpiece coordinate space 38 is determined, a model of the cutting portion 102 in the cutting portion coordinate space 40 can be mapped to the subject coordinate space 36.

The pose tracking system 60 can track the pose of the at least two target markers 62, 64 at a sufficiently high accuracy and sufficiently low latency for the targeted application of the system. In some embodiments, the pose tracking system 60 can include a detection device 66 for tracking the at least two target markers 62, 64, a processor operatively coupled to the detection device 66, and a computer-readable memory operatively coupled to the processor. The detection device 66 can be a stereoscopic video camera.

In some embodiments, the pose tracking system 60 can be an optical pose tracking system, for example, the Micron-Tracker™ by ClaroNav™ Inc. When the pose tracking system 60 is an optical pose tracking system, the at least two target markers 62, 64 can include high contrast optical markings as shown in FIG. 1. The target markers 62, 64 can be referred to as "optical markers" when they include high contrast optical markings. Although FIG. 1 shows three high contrast optical markings on each of the first target marker 62 and the second target marker 64, in some embodiments, each of the first target marker 62 and the second target marker 64 can include fewer or more high contrast optical markings.

In some embodiments, each of the at least two target markers 62, 64 can include one or more retro-reflective regions and the optical pose tracking system can include a tracking camera and a source of illumination placed near the lenses of the tracking camera such that a contrast between the surface of the retro-reflective region and the surrounding surfaces is created in the camera's image. The one or more retro-reflective regions can have any appropriate shape, including a spherical shape. In other embodiments, a magnetic tracking system may be used and the at least two target markers 62, 64 may contain a magnetic field sensing coil. In some embodiments, the pose tracking system 60 may be an electromagnetic pose tracking system.

Prior to a medical procedure, a user may plan a cutting region 32 within the surgical subject 30. The cutting region 32 can be any region that the user desires to cut, incise, or slit using the cutting portion 102 of the surgical instrument 100. The cutting region 32 may also be referred to as a cutting path, a planned path, or a desired path. For example, the tooltip of a cutting portion 102 can be a saw and the cutting region 32 can be a cutting path for the saw or a cutting plane identifying a desired depth and angle within which to cut into the surgical subject 30.

For another example, the tooltip of a cutting portion 102 can be a burr and the cutting region 32 can be a three dimensional (3D) volume to be removed from the surgical subject 30, such as a knee to receive a knee transplant. In at least one embodiment, the cutting region 32 can be a rectangular prism. The burr on the surgical instrument 100 may follow the cutting region 32 to remove the 3D volume (i.e., the rectangular prism) from the surgical subject 30.

In some embodiments, the cutting region 32 may be a cutting path substantially symmetrically distributed about a central axis. For example, as shown in FIG. 1, the cutting region 32 is a cutting path for a hole that the user wishes to drill when preparing for a dental implant. The cutting region 32 can be used to determine a desired pose of the cutting portion 102 required to achieve the cutting region 32. Furthermore, a geometrical descriptor of the cutting region 32 can be used to determine the desired pose.

The controller 50 is operatively coupled to the handpiece 100 for electronic communication. The controller 50 can include a processor (not shown in FIG. 1) and a computer-readable memory (not shown in FIG. 1) operatively coupled to the processor. The computer-readable memory of the controller 50 can store the geometrical descriptor of the cutting region 32. In at least one embodiment, the controller 50 can be operatively coupled to the pose tracking system 60. In at least one embodiment, the controller 50 can include the pose tracking system 60.

The controller 50 can be configured to map the cutting pose of the cutting portion 102 reported by the pose tracking system 60 to the subject coordinate space 36. Furthermore, the controller 50 can be configured to determine deviations between the cutting pose of the cutting portion 102 in the subject coordinate space 36 and the desired pose of the cutting portion 102 in the subject coordinate space 36 determined from the geometrical description stored in the computer-readable memory. That is, the controller 50 can be configured to map deviations between planned path 32 and the current position and orientation of the cutting portion 102.

The deviations between the cutting pose and the desired pose can be displayed graphically. The deviations between the cutting pose and the desired pose can include a plurality of degrees of freedom. In particular, deviations can include angular deviations (i.e., tilt, roll, and yaw), positional deviations (i.e., x-axis and y-axis, or lateral axis and longitudinal axis), and depth deviations (i.e., z-axis). For example, there can be 6 degrees of deviation between the cutting pose and the desired pose of a saw. For another example, since the cutting volume of a rotating drill is rotationally symmetric, the drill's rotation angle around its longitudinal axis (i.e., yaw) is unimportant. Thus, only 5 degrees of deviation between the cutting pose and the desired pose are important for a rotating drill.

In some embodiments, the geometrical descriptor is defined relative to an image of the anatomical region 30. The controller 50 can be further configured to compute a registration mapping between the image and the subject coordinate space 36, and to use that registration mapping in determining the deviations.

Figure 2:
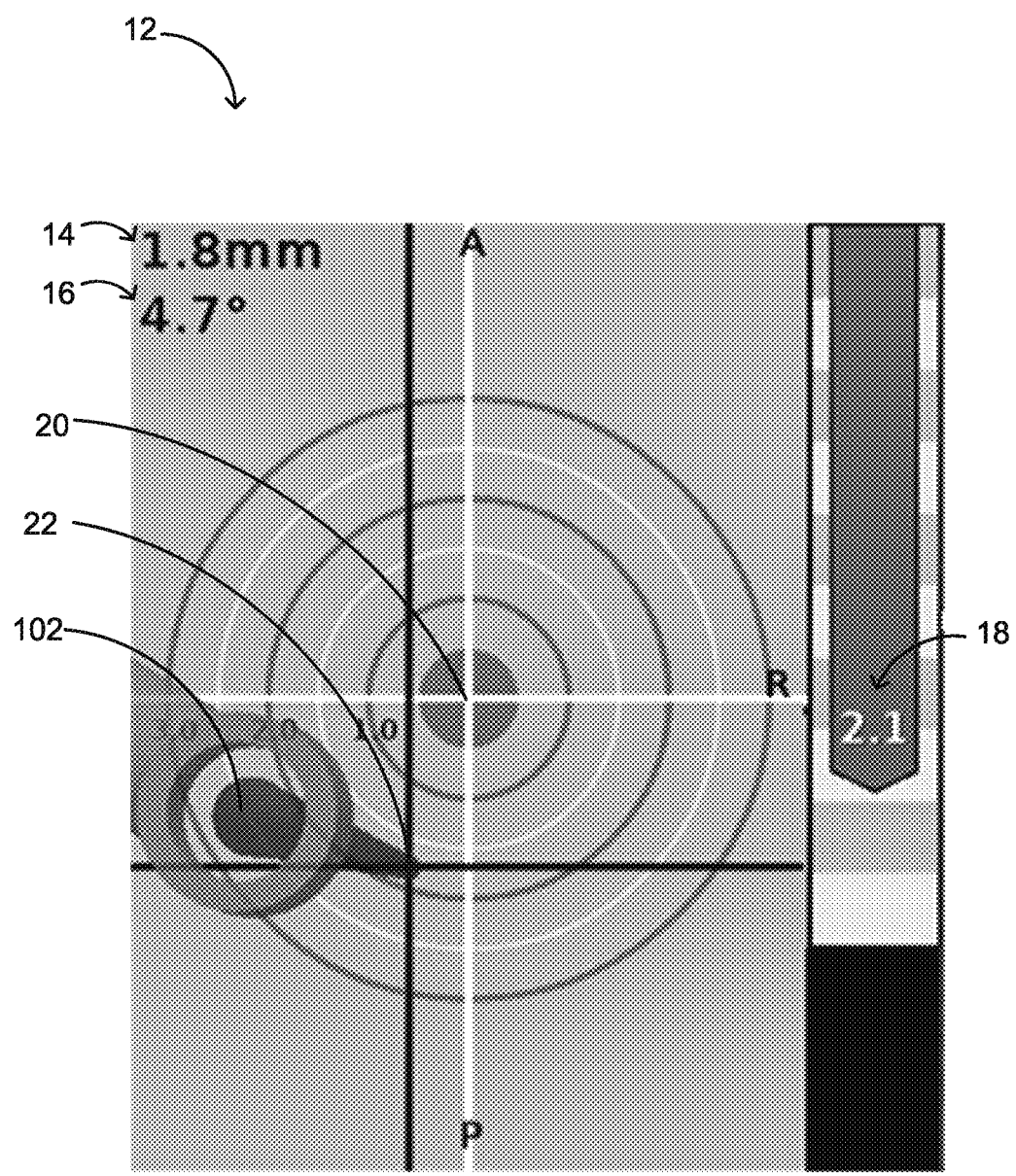
FIG. 2 is an example illustration of a display for the system of FIG. 1.

Referring now to FIG. 2, shown therein is an example illustration of a display 12 of the system of FIG. 1, according to at least one embodiment. The display 12 can be a guidance graphical display of a dental navigation system, such as Navident® by ClaroNav Inc. The tooltip of the cutting portion 102 is represented in display 12 as a cone inserted in a surgical instrument in display 12.

Axis 22 illustrates the current position of the tooltip of the cutting portion 102. Display 12 indicates the positional deviation 14 and the angular deviation 16 between the axis 22 and the planned drilling axis 20 on the jaw image. For example, as shown in FIG. 2, display 12 indicates a distance 14 of 1.8 millimeters (mm) between the tip of the drill bit and the planned drilling axis 20, and an angular deviation 16 of 4.7° between the drill bit's axis and the planned drilling axis 20. The end of the tooltip of the cutting portion 102 along the drilling axis 20 is shown in a bar on the right. Display 12 indicates the depth deviation 18 between the end of the tooltip of the cutting portion 102 and the planned drilling depth on the jaw image. For example, as shown in FIG. 2, display 12 indicates a depth deviation 18 of 2.1 millimeters (mm).

With deviations between the cutting pose and the desired pose graphically shown in display 12, the user can use the display 12 to control the motion of the surgical instrument 100. In particular, the user can review the data presented on the display 12 and move their hand to reduce or minimize the deviations while traversing the cutting region 32. That is, display 12 can guide a user to accurately implement a cutting or drilling plan in a subject jaw. For example, a user may attempt to drill in a subject jaw in preparation for the subsequent placement of an implant using a handpiece 100 having a cutting portion 102 with a tooltip that is a drill bit. The user can manipulate the handpiece 100 and try to maintain both of the positional deviation 14 and the angular deviation 16 at 0 while drilling in the jaw bone to incrementally reduce the depth deviation 18 towards 0, then stop immediately. In at least one embodiment, the user may stop the drilling once the computer 50 indicates that the planned depth is reached (e.g., depth deviation 18 of 0).

While it can be easy to align the cutting pose with the desired pose at a coarse level, the level of drilling accuracy typically desired requires finer hand control, which can be very challenging for many users. For example, bringing the tooltip of the cutting portion 102 into close proximity (i.e., positional deviation 14 less than 2 mm and angular deviation 16 less than 10°) to the planned cutting path 32 is relatively easy for users.

However, the desired accuracy is typically a positional deviation 14 of less than 0.3 mm and an angular deviation 16 of less than 1°. Such a desired accuracy requires fine hand adjustments, which are much more difficult to achieve. Keeping track of, and correcting, 5 or 6 independent deviations using very fine hand motions (sub-mm and sub-degree) presents a major challenge to the user. Furthermore, due to the nearly perpendicular relationship between the handle 106 and the cutting portion 102 of the handpiece 100, the user must also mentally translate between the positional, angular, and depth deviations 14, 16, and 18 indicated on display 12 and the corrective motion that needs to be applied to the handle 106. A substantial amount of training and skill may be necessary to overcome this challenge.

To assist the user in achieving the desired accuracy, the controller 50 is also configured to activate adjustment motors in the surgical instrument 100 to reduce the deviations. That is, the controller 50 can activate the adjustment motors to control the motion of the tooltip. For example, the controller 50 can control two actuators to adjust the drilling axis angle in tilt and roll to reduce the angular deviation to be below 1°, leaving the user to manually correct only the positional deviation. In another example, in the case of a cutting portion 102 having a burr to remove a desired volume, the plurality of adjustment motors can control the burr so that it automatically removes the desired volume. With the controller 50 controlling the adjustment motors to automatically reduce the deviations between the cutting pose and the desired pose in a planned burr motion path, a user may only need to apply a force on handle 106 against the anatomy being modified to perform the cutting.

In at least one embodiment, the amount of deviation that the surgical instrument 100 can correct is limited. For example, the surgical instrument 100 may only correct positional deviations 14 of up to 2 millimeters (mm) in each dimension (i.e., x-axis and y-axis, or lateral axis and longitudinal axis) and/or angular deviations 14 (i.e., tilt and roll) of up to 10°. In such a case, the display 12 can indicate the deviations between an imaginary pose of the cutting portion 102 when each adjustment motor is set to a position in approximately the middle 20% of its operating range and the desired pose of the cutting portion 102. This can help the user correct the position and orientation of the handle 106 as needed to prevent one or more of the adjustment motors from reaching its operating limit.

Figure 3:
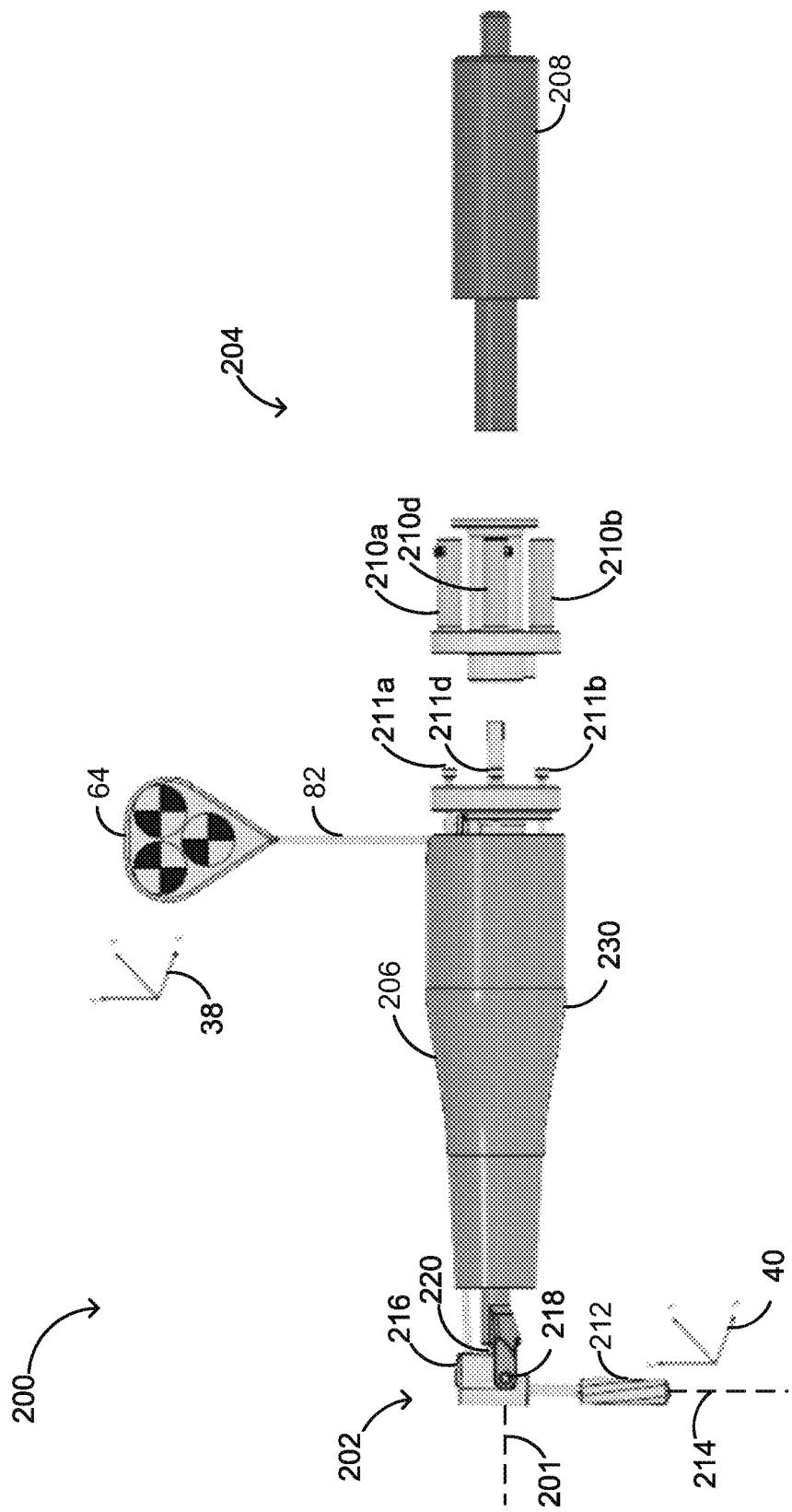
FIG. 3 is an example illustration of a surgical instrument of the system of FIG. 1, according to at least one embodiment.

Referring now to FIG. 3, shown therein is an exploded view of a portion of an example illustration of a surgical instrument 200, according to at least one embodiment. The surgical instrument 200 can be used in a surgical navigation system such as surgical navigation system 10 of FIG. 1. The surgical instrument 200 is shown as having a longitudinal axis 201. The surgical instrument 200 includes a cutting portion 202 and a body 204 having a handle 206.

The body 204 includes the at least one actuator. In particular, the body 204 includes a drive motor 208 and a plurality of adjustment motors 210a, 210b, 210c (not shown in FIG. 1) and 210d (herein referred to collectively as 210). The drive motor 208 can be used for driving the cutting portion 202 in at least one of a rotating, a reciprocating, and a vibrating motion. The drive motor 208 can be coupled to a driveshaft 220, which is further coupled to the cutting portion 202. The driveshaft 220 transmits torque from the drive motor 208 to the cutting portion 202, that is, the driveshaft 220 drives the cutting portion 202.

In at least one embodiment, the plurality of adjustment motors 210 can be small in diameter. For example, the adjustment motors 210 can have a diameter of less than 6 millimeters (mm). An example of such a motor is Maxon™ EC4 by Maxon Motor Ag™. In at least one embodiment, the adjustment motors can be brushless motors geared down at a high ratio to provide sufficient torque for overcoming forces acting against adjustments during surgery. For example, the gear ratio can be 1:100 or higher.

Power and control signals can be transmitted from controller 50 to the at least one actuator. Furthermore, positional signals can be transmitted from the plurality of at least one actuator to the controller 50. The positional signals can be provided by encoders on the at least one actuator. The positional signals can enable the controller 50 to compute the mapping between the cutting portion 202 and the target marker 64 tracked by pose tracking system 60.

For simplicity, the power, control signals, and positional signals to and from the at least one actuator are not shown. Power can be provided through electrical cables or wireless communication. In some embodiments, it can be desirable to have a power source that connects to multiple kinds of surgical instruments. For example, dental implantation drilling motors may use a standard surgical instrument interface called "E-Type" connection. In some embodiments, the surgical instrument 200 can have an E-Type connection. There may be a standard E-Type connection to the drive motor 208 at one end, and a detachable coupling (not shown) to the handle 206 and cutting portion 202 at the opposite end. The detachable coupling can allow for ease of connection and disconnection between the drive motor 208 and the handle 206.

The plurality of adjustment motors 210 are coupled to the surgical instrument 200 through a plurality of motor couplers 211a, 211b, 211c (not shown in FIG. 1), and 211d (herein referred to collectively as 211). Each adjustment motor 210 can have a corresponding motor coupler 211. The plurality of adjustment motors 210 are operatively coupled to the controller 50.

The plurality of motor couplers 211 transmit torque generated by each of the adjustment motors 210 to mechanisms within passive assembly 230. The mechanisms within passive assembly 230 convert torque into motion in one of the degrees of freedom of the cutting portion 202. The passive assembly 230 is located within the body 204 of surgical instrument 200. While the passive assembly 230 is shown in FIG. 3 as being located within the handle 206 portion of the body 204, in at least one embodiment, the passive assembly 230 may not be located in the handle 206 portion of the body 204.

As shown in FIG. 3, the body 204 can have a pivotable attachment 218 to attach the cutting portion 202 to the body 204. The pivotable attachment 218 may be any mechanism capable of providing a pivotable motion to the cutting portion 202. For example, as shown in FIG. 3, the pivotable attachment 218 is a hinge.

The cutting portion 202 can include a head 216 and a tooltip attached to the head 216. As shown in FIG. 3, the pivotable attachment 218 can attach to the head 216 of the cutting portion 202. As a result, the head 216 is coupled to at least one of the mechanisms coupled to the adjustment motors 210.

As shown in FIG. 3, the tooltip can be a drill bit 212 rotatable about a drilling axis 214. The drive motor 208 can drive the drill bit 212 in a rotating motion about the drilling axis 214. With a drill bit 212 as a tooltip, the geometrical descriptor can be a linear drilling path 32. With a linear drilling path 32, the deviations between the cutting pose and the desired pose can contain two angles of difference in orientation between the drilling axis 214 and the drilling path 32. That is, the cutting pose and the desired pose can include two angular deviations, namely tilt and roll. In addition, the deviations between the cutting pose and the desired pose may contain a 2-dimensional (2D) translation vector describing the difference between a location on the drilling axis 214 and a location on the drilling path 32. That is, the cutting pose and the desired pose can include two positional deviations, namely along a lateral axis and a longitudinal axis.

Also shown in FIG. 3, pole 82 attaches the second target marker 64 to the body 204 of the surgical instrument 200. Changes in the pose of the second target marker 64 are indicative of the changes in the pose of the part of the body 204 of the surgical instrument 200 within a handpiece coordinate space 38. The cutting portion 202 in the cutting portion coordinate space 40 can be mapped to the subject coordinate space 36 based on the geometrical relationship between the cutting portion 202 and the handpiece 200, including the states of the drive motor 208 and the plurality of adjustment motors 210.

Figure 4A:
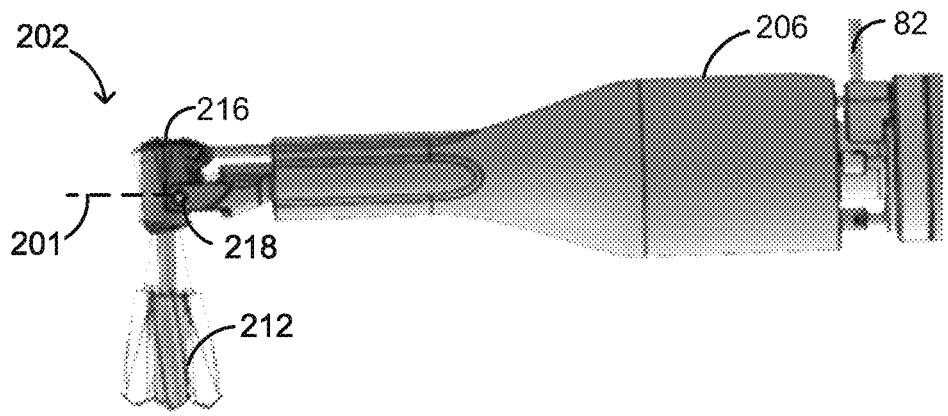
FIG. 4A is an example illustration of a tilt motion of the cutting portion of the surgical instrument of FIG. 3, according to at least one embodiment.
Figure 4B:
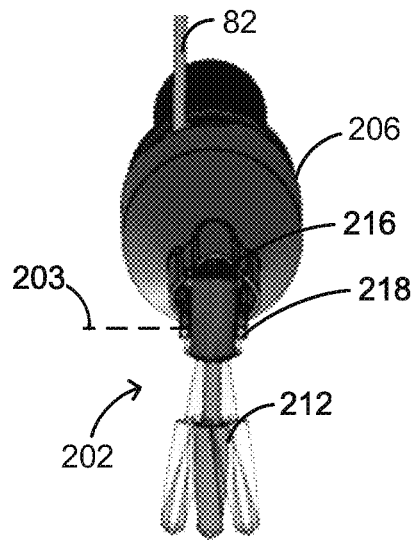
FIG. 4B is an example illustration of a roll motion of the cutting portion of the surgical instrument of FIG. 3, according to at least one embodiment.
Figure 4C:
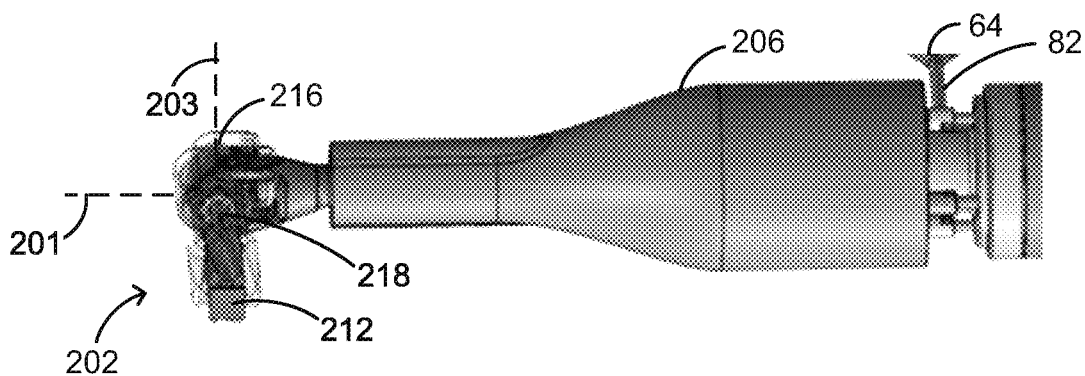
FIG. 4C is an example illustration of a pan motion of the cutting portion of the surgical instrument of FIG. 3, according to at least one embodiment.

Referring now to FIGS. 4A, 4B, and 4C, shown therein are example illustrations of tilt, roll, and pan motions of the cutting portion of the surgical instrument of FIG. 3, according to at least one embodiment. As described above, the head 216 is mechanically connected to the handle 206 such that the head 216 can move in a plurality of degrees of freedom. For example, head 216 can vary in four degrees of freedom such as tilt, roll, longitudinal-pan motion, and lateral-pan motion with respect to the handle 206.

The plurality of adjustment motors 210 control the motion between the head 216 and the handle 206. The passive assembly 230 within the handle 206 converts torque generated by the plurality of adjustment motors 210 into motion in one of the degrees of freedom illustrated in FIGS. 4A, 4B, 4C, namely a tilt motion, a roll motion, and pan motions (i.e., translational motion). In at least one embodiment, each adjustment motor 210 can control a single degree of freedom in the plurality of degrees of freedom of the surgical instrument 200. In some embodiments, pluralities of adjustment motors 210 can control a plurality of degrees of freedom in coordinated integrated motions.

The tilt motion of the head 216 is a rotation about a transverse axis 203 (i.e., tilt axis) (shown in FIG. 4B) of the surgical instrument 200. In other words, the head 216 tilts forward and backward along the longitudinal axis 201 (i.e., roll axis) of the surgical instrument 200, as shown in FIG. 4A. The roll motion of the head 216 is rotation about the longitudinal axis 201 (shown in FIG. 4A) of the surgical instrument. In other words, the head 216 rolls left and right along the transverse axis 203 of the surgical instrument 200, as shown in FIG. 4B.

The longitudinal-pan motion of the head 216 includes translation forward and backward along the longitudinal axis 201 of the surgical instrument 200, as shown in FIG. 4C. The lateral-pan motion of the head 216 includes translation left and right along the transverse axis 203 of the surgical instrument 200, as shown in FIG. 4C.

The plurality of adjustment motors 210 can be used for adjusting a cutting pose of the cutting portion 202 relative to the handle 206 in at least one degree of freedom. In some embodiments, the adjustment motors 210 can adjust the cutting pose of the cutting portion 202 in a plurality of degrees of freedom. For example, the plurality of adjustment motors 210 can adjust the cutting pose of the cutting portion 202 by at least one of tilting, rolling, and translating the cutting portion 202. In at least one embodiment, the plurality of adjustment motors 210 can adjust the cutting pose of the cutting portion 202 by a combination of tilting, rolling, and translating the cutting portion 202.

The controller 50 can activate the adjustment motors 210 to reduce the deviations measured between the cutting pose of the cutting portion 202 and a desired pose of the cutting portion 202. For example, if the desired cutting pose is at an angle of 6 degrees, the controller 50 can actuate the plurality of adjustment motors 210 to adjust the cutting pose to be 6 degrees to follow the planned path 32.

Furthermore, the plurality of adjustment motors 210 can adjust the cutting pose of the cutting portion 202 to reduce the deviations while the user applies a force to the cutting portion 202. A user can apply a force to the cutting portion 202 in order to perform the cutting or drilling. The plurality of adjustment motors 210 can account for deviations despite a range of applied forces. For example, the force may be around 5 Newtons (N) applied to the cutting portion 202 in a direction opposing the adjustment.

Figure 5:
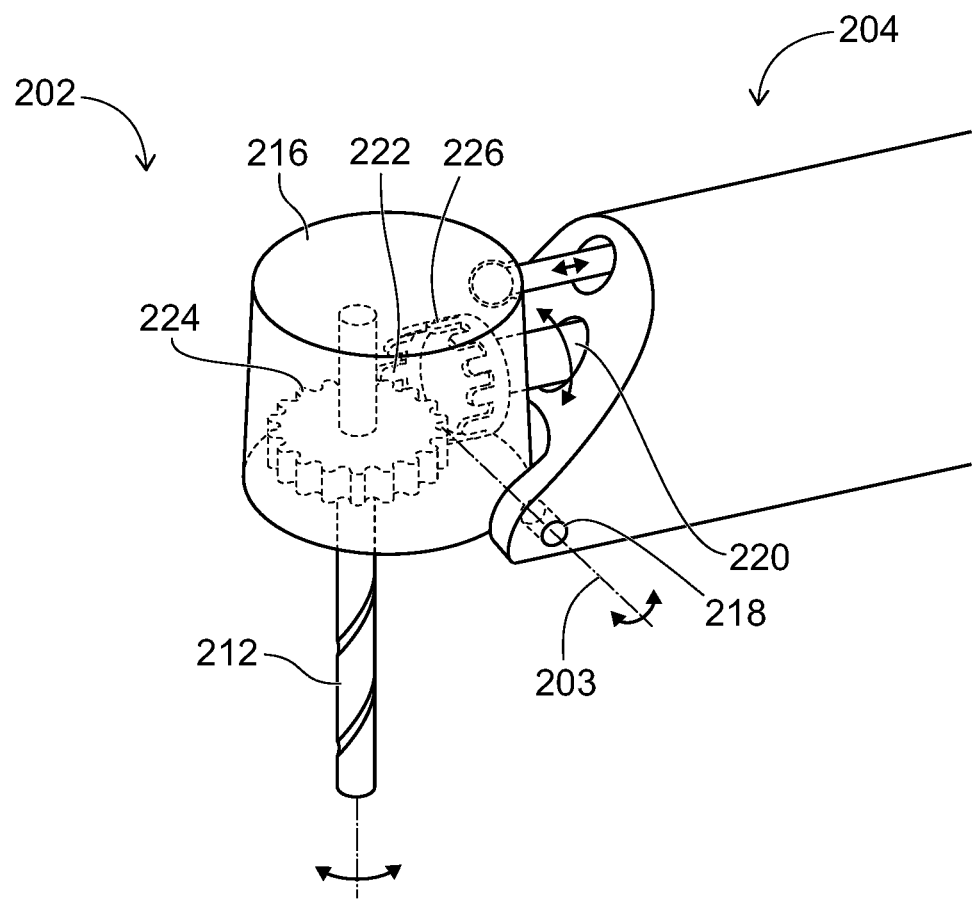
FIG. 5 is an example illustration of a drive torque transmission mechanism of the surgical instrument of FIG. 3, according to at least one embodiment.

Referring now to FIG. 5, shown therein is an example illustration of a drive torque transmission mechanism of the surgical instrument of FIG. 3, according to at least one embodiment. While the cutting portion 202 is attached to the pivotable attachment 218 of the body 204 the driveshaft 220 can transmit torque from the drive motor 208 (not shown in FIG. 5) to the cutting portion 202 within a contact region 222.

The contact region 222 is formed by the head 202 and the body 204. In particular, the contact region 222 can include a cutting portion contact surface 224 of the head 216 and a torque transmission surface 226 of the body 204. As shown in FIG. 5, each of the cutting portion contact surface 224 and the torque transmission surface 226 can also be a sprocket. The torque transmission surface 226 can transmit the torque generated by drive motor 208 to tooltip 212 via sprocket 224.

The cutting portion contact surface 224 can be coupled to the cutting portion 202 to drive the cutting portion 202. The torque transmission surface 226 can be coupled to the driveshaft 220 to be driven by the driveshaft 220. The torque transmission surface 226 can contact the cutting portion contact surface 224 to transfer torque thereto. The cutting portion contact surface 224 and the torque transmission surface 226 can remain in contact through a range of adjustments in the plurality of degrees of freedom to transmit torque from the drive motor 208 to the cutting portion 202.

Head 216 can be connected to the passive assembly 230 (not shown in FIG. 5) through pivotable attachment 218. Pivotable attachment 218 can be positioned so that it rotates about the transverse axis 203 and passes through the contact region 222 between the cutting portion contact surface 224 and the torque transmission surface 226. Thus, the contact region 222 between the cutting portion contact surface 224 and the torque transmission surface 226 can be maintained while the head 216 tilts through its full tilt adjustment range. In at least one embodiment, the tilt adjustment range of the head can be −10° to 20°.

In at least one embodiment, the tilt adjustment range is within 20° of the tilt angle in the unadjusted pose, the roll adjustment range is within 20° of the roll angle in the unadjusted pose, and/or the translation range for a pair of head translation motors is within 2 mm of the unadjusted pose.

Figure 6:
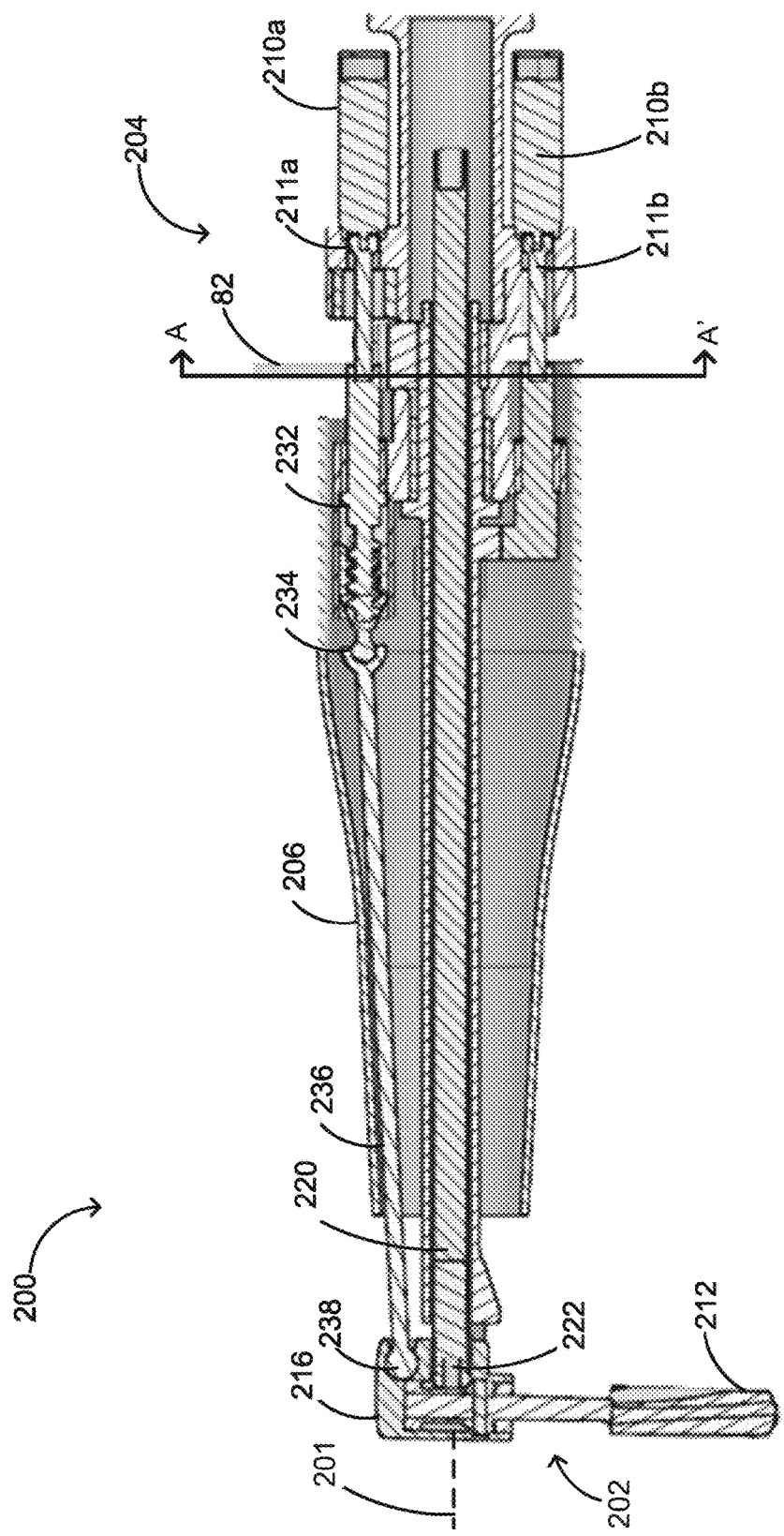
FIG. 6 is an example illustration of a tilting mechanism of the surgical instrument of FIG. 3, according to at least one embodiment.

Referring now to FIG. 6, shown therein is an example illustration of a tilting mechanism of the surgical instrument of FIG. 3, according to at least one embodiment. In the example shown in FIG. 6, the plurality of adjustment motors 210 include adjustment motor 210a (i.e., head translation motor) connected to the cutting portion 202 and configured to rotate or tilt the cutting portion 202 relative to the handle 206 around the transverse axis 203 (shown in FIG. 4B). The transverse axis 203 is substantially perpendicular to both the longitudinal axis 201 and a lateral adjustment direction (shown in FIG. 4C).

The adjustment motor 210a can be coupled to the motor coupler 211a. The motor coupler 211a can be further coupled to a tilt screw 232. The tilt screw 232 can be further coupled to a first ball joint 234. The first ball joint 234 can be further coupled to a tilt link 236. The tilt link 236 can be further coupled to a second ball joint 238. The second ball joint 238 can be further coupled to the head 216.

During operation, the adjustment motor 210a can rotate the motor coupler 211a, which in turn, can rotate the tilt screw 232. Rotating the tilt screw 232 can cause the first ball joint 234 to push or pull the tilt link 236. Pushing or pulling the tilt link 236 can cause the tilt link 236 to translate longitudinally along the longitudinal axis 201 of the surgical instrument 200. Longitudinally translating the tilt link 236 can cause the second ball joint 238 to push or pull on the head 216, which in turn, can cause the head 216 to tilt forward or backward respectively around the transverse axis 203. For example, when the adjustment motor 210a rotates the tilt screw 232 forwards (e.g., towards the head 216), the head 216 can tilt downwards. When the adjustment motor 210a rotates the tilt screw 232 backwards (e.g., away from the head 216), the head 216 can tilt upwards.

Figure 7:
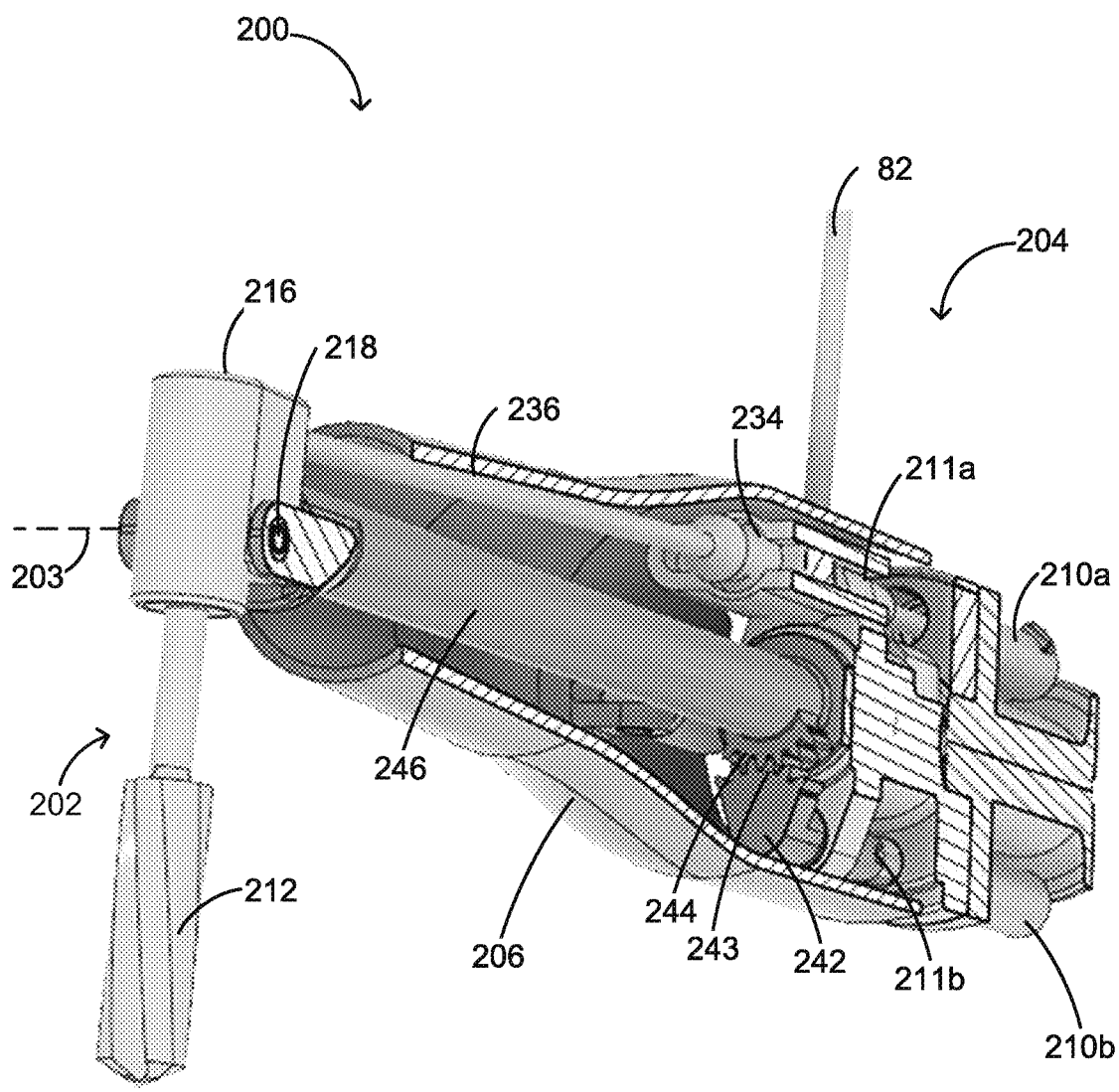
FIG. 7 is an example illustration of a rolling mechanism of the surgical instrument of FIG. 3, according to at least one embodiment.

Referring now to FIG. 7, shown therein is an example illustration of a rolling mechanism of the surgical instrument of FIG. 3, according to at least one embodiment. In the example shown in FIG. 7, the plurality of adjustment motors 210 include adjustment motor 210b (i.e., roll adjustment motor) connected to the cutting portion 202 and configured to rotate the cutting portion 202 relative to the handle 206 around the longitudinal axis 201 (shown in FIG. 4A). The longitudinal axis 201 is substantially perpendicular to the transverse axis 203 and substantially coincident to the longitudinal axis of the driveshaft 220 (shown in FIG. 4C).

The adjustment motor 210b can be coupled to the motor coupler 211b. The motor coupler 211b can be further coupled to a first roll sprocket 242. The first roll sprocket 242 can be further coupled to a second roll sprocket 244. The first and second roll sprockets 242 and 244 can be further coupled at a roll contact region 243. The second roll sprocket 244 can be further coupled to a shaft 246. The shaft 246 can be further coupled to the head 216 through the pivotable attachment 118. The shaft 246 can be positioned around the driveshaft 220 (shown in FIG. 6) such that rotation of either the shaft 246 or the driveshaft 220 does not cause the other to move.

During operation, the adjustment motor 210b can rotate the motor coupler 211b, which in turn, can rotate the first roll sprocket 242. Rotating the first roll sprocket 242 can rotate the second roll sprocket 244, which in turn, can rotate the shaft 246 and cause the head 216 to roll. Rotating the motor coupler 211b in a first direction can cause the head 216 to roll in a first direction about the longitudinal axis 201. Rotating the motor coupler 211b in a second direction can cause the head 216 to roll in a second direction about the longitudinal axis 201.

In at least one embodiment, the body 204 includes a head support shaft (not shown in FIG. 7), the head 216 being pivotably attached to the head support shaft by the pivotal attachment 218. The plurality of adjustment motors 210 may also include a roll adjustment motor 210b connected to the head support shaft for rotating the head support shaft about longitudinal axis 201 to rotate the cutting portion 202 about the longitudinal axis 201.

Figure 8:
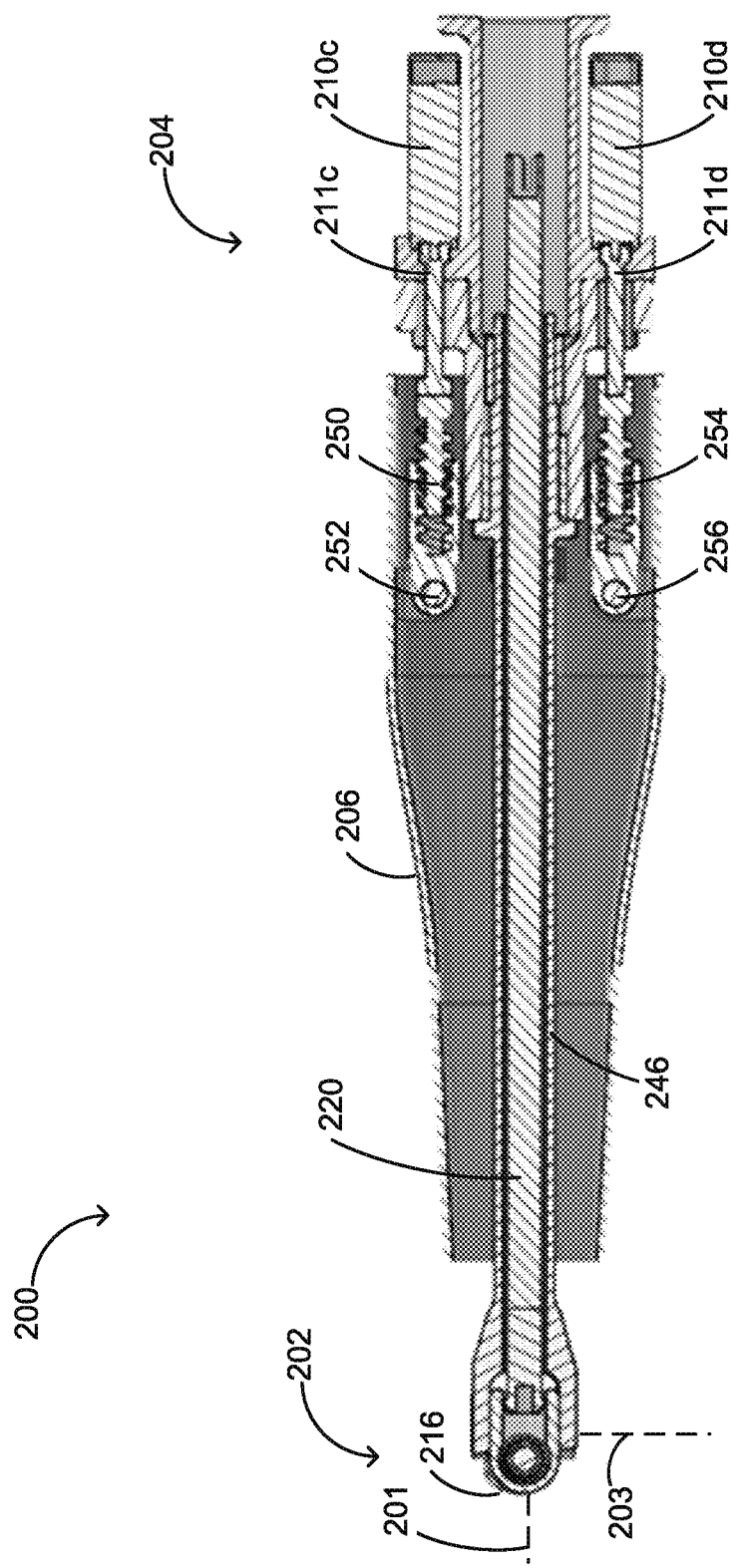
FIG. 8 is an example illustration of a mechanism for a pan motion of the cutting portion of the surgical instrument of FIG. 3, according to at least one embodiment.

Referring now to FIG. 8, shown therein is an example illustration of a mechanism for a pan motion of the cutting portion of the surgical instrument of FIG. 3, according to at least one embodiment. The pan motion of the head 216 includes translation along the longitudinal axis 201 and the transverse axis 203 of the surgical instrument 200. Two adjustment motors 210c and 210d are coupled to motor couplers 211c and 211d, respectively. The motor coupler 211c can be further coupled to a first pan screw 250. The first pan screw 250 can be further coupled to a first pan joint 252. The first pan joint 252 can be further coupled to the shaft 246. Similarly, the motor coupler 211d can be further coupled to a second pan screw 254. The second pan screw 254 can be further coupled to a second pan joint 256. The second pan joint 256 can be further coupled to the shaft 246. As described above, the shaft 246 can be further coupled to the head 216 through the pivotable attachment 218 (not shown in FIG. 8).

During operation, the adjustment motors 210c and 210d can rotate the pan screws 250 and 252 through the motor couplers 211c and 211d, respectively. Rotating the pan screws 250 and 252 can cause the first and second pan joints 252 and 256 to translate. In at least one embodiment, the first and second pan joints 252 and 256 can translate independently from one another. In at least another embodiment, the first and second pan joints 252 and 256 can translate in parallel with one another.

The relative motion between the pan joints 252 and 256 can cause the head 216 to pan in various directions. For example, referring to FIG. 8, to pan the head 216 in a first direction along the transverse axis 203, the adjustment motor 210c can cause the first pan joint 252 to translate forward along the longitudinal axis 201 while the adjustment motor 210d remains stationary. The first pan joint 252 can translate forwards, causing shaft 246 to pan head 216 in a first direction along the transverse axis 203. Similarly, when adjustment motor 210d causes the second pan joint 256 to translate forward along the longitudinal axis 201 while the adjustment motor 210c remains stationary, the head 216 can pan in a second direction along the transverse axis 203.

When the motors 210c and 210d translate the pan joints 252 and 256 rearward along the longitudinal axis 201, the opposite pan motion will occur. To translate the head 216 along the longitudinal axis 201, motors 210c and 210d work in parallel to translate the pan joints 252 and 256 the same distance in the same direction. For example, if both motors 210c and 210d translate the pan joints 252 and 256 a first distance forward along the longitudinal axis 201, the head 216 will translate forward along the longitudinal axis 201. When both motors 210c and 210d translate the pan joints 252 and 256 a second distance rearward along the longitudinal axis 201, the head 216 will translate rearward along the longitudinal axis 201. Thus, the adjustment motors 210c and 210d can allow the head 216 to pan longitudinally and transversely.

Figure 9:
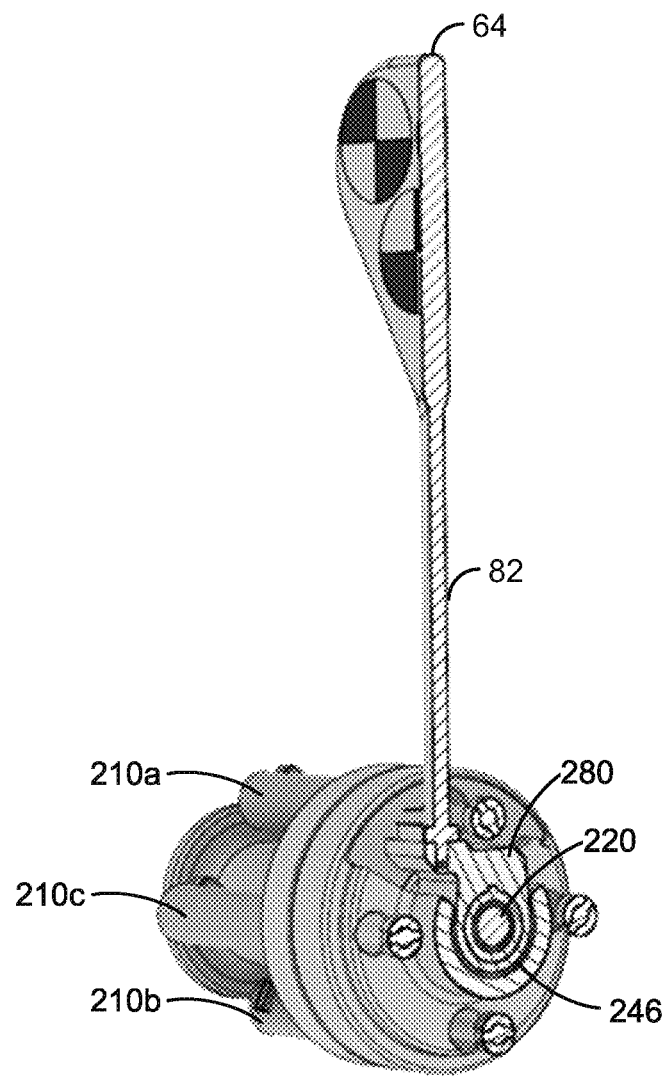
FIG. 9 is an example illustration of a cross-sectional view of the surgical instrument and the second target marker of FIG. 3, according to at least one embodiment.

Referring now to FIG. 9, shown therein is an example illustration of a cross-sectional view of the surgical instrument and the second target marker of FIG. 3 along plane A-A' (shown in FIG. 6), according to at least one embodiment. The pole 82 attaches the second target marker 64 to sleeve 246 through bracket 280. In at least one embodiment, the second target marker 64 can track the pose of the cutting portion 202 by measuring the pose of sleeve 246, which is indicative of the roll and pan of the head 216, and the tilt of the head 216 can be calculated using the positions of the tilt screw 232 and the first roll sprocket 242, which can be tracked by computer 50. The tilt screw 232 and the first roll sprocket 242 can be tracked, for example, by using encoders on the shafts driving their motion (not shown in FIG. 9). The tilt angle of the head 216 can be a function of the position of the tilt screw 232 and the first roll sprocket 242. The tilt angle of the head 216 can be obtained experimentally through a calibration process and stored in computer-readable memory accessible to the controller 50.

Figure 10:
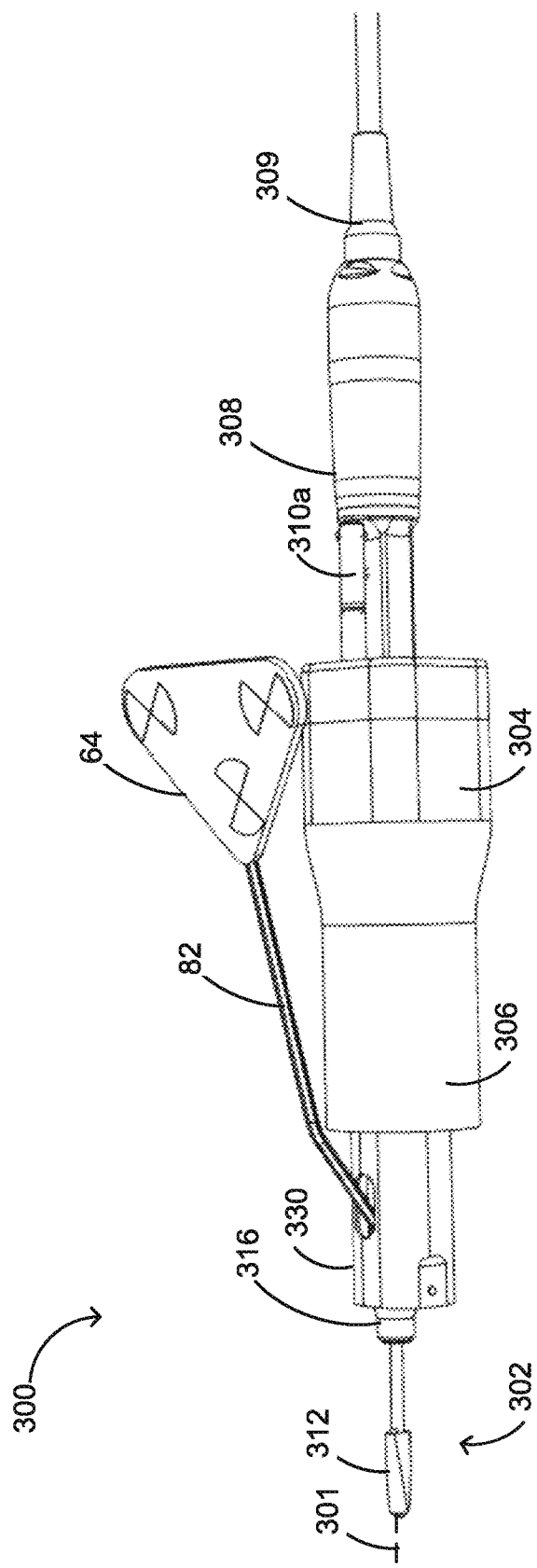
FIGS. 10 and 11 are example illustration of another surgical instrument of the system of FIG. 1, according to at least one embodiment.

In some embodiments, such as that shown in FIG. 10, the head 216 can be tracked directly, eliminating the need for separate sensing of the tilt angle.

In existing surgical navigation systems, marker 64 can be coupled to the tool handle 206. While it may be possible to compute the pose of the tooltip of the cutting portion 202 by combining the measurement of the pose of the handle 206 with measurements of the positions of each of the adjustment actuators, it is preferred to track the head 216 directly or by tracking sleeve 246 and combining it with a single addition tilt measurement. This can eliminate inaccuracies caused by slack, or "play", in any of the couplers and joints, or wear in any contact points between the handle 206 and the tooltip 212 of the cutting portion 202, thus providing a more accurate computation of the deviations between the actual and the desired poses of tooltip 212.

In at least one embodiment, the adjustment motors 210 can be detachable from the surgical instrument 200. Typically, the surgical instrument 200 needs to be steam-sterilized between uses to prevent transmission of infections between patients. Since the adjustment motors 210 can be damaged by the harsh sterilization process, it is preferable to separate the plurality of adjustment motors 210 from the passive assembly 230 of the surgical instrument 200. For example, it can be desirable to separate the adjustment motors 210 from the handle 206 and the cutting portion 202. The adjustment motors 210 can be detached such that the handle 206 and the cutting portion 202 can be steam sterilized without sterilizing the adjustment motors 210.

In at least one embodiment, the surgical instrument 200 can have at least one seal (not shown in FIGS. 3 to 9). The seal can enable the surgical instrument 200 to be thoroughly cleaned and sterilized between uses. Furthermore, internal parts of the surgical instrument 200 can be damaged when exposed to fluids present in the oral cavity during surgery, such as blood and saliva. In at least one embodiment, the seal can encapsulate the surgical instrument 200, except for the tooltip 212. In at least one embodiment, the seal can be a silicon rubber sleeve that can withstand steam sterilization. In at least one embodiment, the seal can be a disposable single-use plastic sleeve.

In some cases, a user may drill through a hard bone. When drilling through a hard bone, the user may apply a force on the handle 206, pushing the tooltip 212 (i.e., a drill bit) against the bone. The surgical instrument 200 needs to transmit this force from the handle 206 to the drill bit 212 while still allowing all degrees of freedom to be controlled as expected. In at least one embodiment, to help transmit the force applied by the user and to reduce distortion, one or more low friction bearings (not shown) may be positioned between the shaft 246 and the handle 206. The bearings may ensure that the tilt link 236 does not contact the handle 206 throughout the full range of motion of all parts of the surgical instrument 200.

Figure 11:
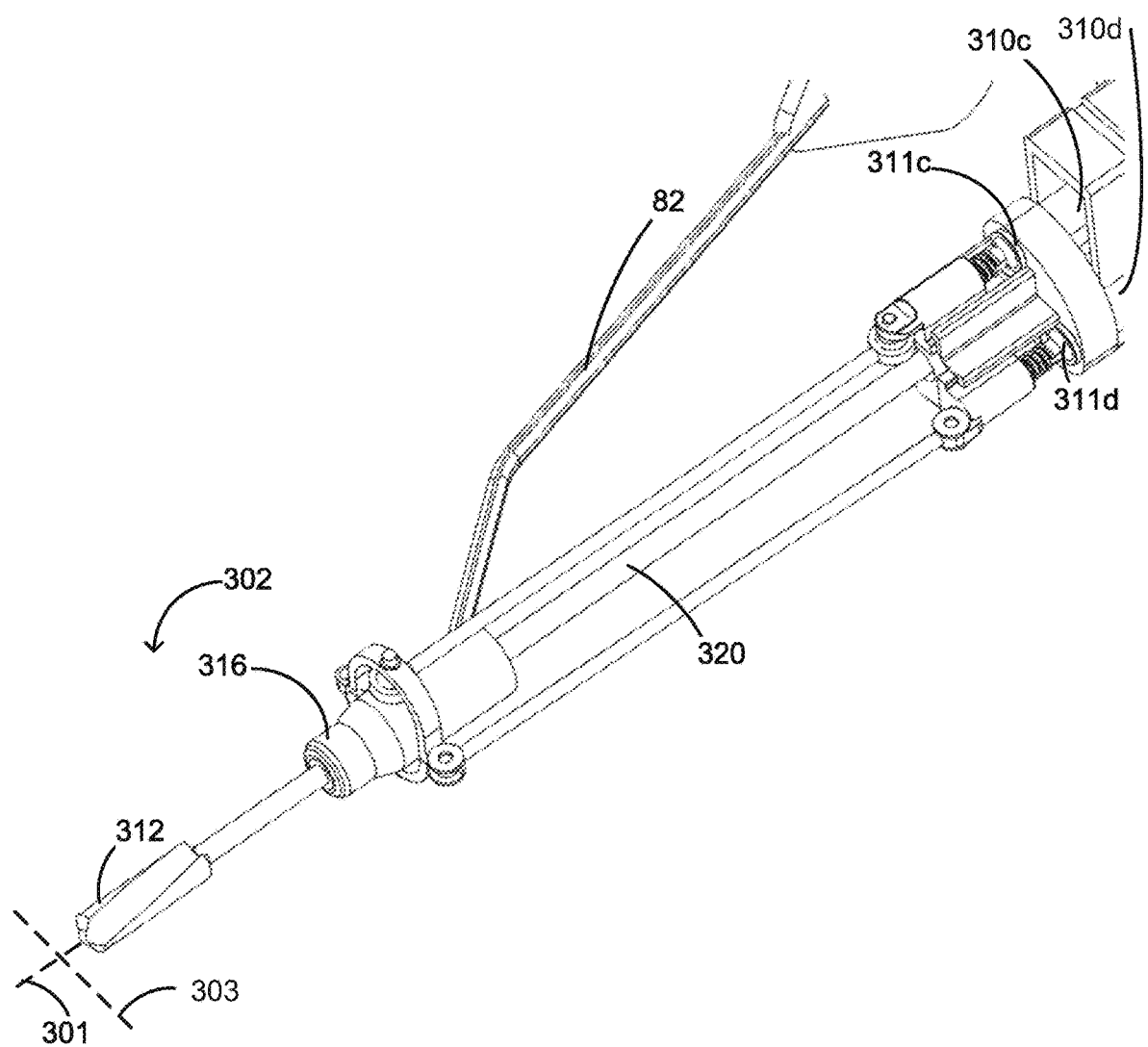

Referring now to FIGS. 10 and 11, shown therein is an example illustration of another surgical instrument 300, according to at least one embodiment. The surgical instrument 300 can be used in a surgical navigation system such as surgical navigation system 10 of FIG. 1. The surgical instrument 300 is shown as having a longitudinal axis 301 passing through the handle 306. The surgical instrument 300 includes a cutting portion 302 and a body 304 having a handle 306.

The drive torque of the surgical instrument 300 is transmitted to a cutting portion 302 along the longitudinal axis 301, which can be convenient in some types of operations, such as side-milling of tooth crowns, or drilling in the spine in preparation for insertion of pedicle screws.

Similar to surgical instrument 200, the body 304 of surgical instrument 300 includes the at least one actuator. In particular, the body 304 includes a drive motor 308 and a plurality of adjustment motors 310a, 310b, 310c, and 310d (shown in FIG. 11) (herein referred to collectively as 310). The drive motor 308 can be used for driving the cutting portion 302 in at least one of a rotating, a reciprocating, and a vibrating motion. The drive motor 308 can be coupled to a driveshaft 320 (shown in FIG. 11), which is further coupled to the cutting portion 302. The driveshaft 320 transmits torque from the drive motor 308 to the cutting portion 302, that is, the driveshaft 320 drives the cutting portion 302.

Similar to surgical instrument 200, power and control signals can be transmitted from controller 50 to the plurality of at least one actuator and positional signals can be transmitted from the plurality of at least one actuator to the controller 50. The positional signals can be provided by encoders on the at least one actuator. The positional signals can enable the controller 50 to compute the mapping between the cutting portion 302 and the target marker 64 tracked by pose tracking system 60 when target marker 64 is not rigidly coupled to cutting portion 302, and/or to inform the controller 50 of how close each adjustment actuator is to the limits of its operating range.

Cable 309 can provide power from the controller 50 to the at least one actuator, provide control signals from the controller 50 to the at least one actuator, and/or provide positional signals from the at least one actuator to the controller 50. In at least one embodiment, at least one of power from the controller 50 to the at least one actuator, control signals from the controller 50 to the at least one actuator, and/or positional signals from the at least one actuator to the controller 50 can be provided wirelessly.

The body 304 of the surgical instrument 300 includes a floating assembly 330 that can move independently from the handle 306. The floating assembly 330 can be coupled to the cutting portion 302. The cutting portion 302 can include a head 316 and a drill bit 312 coupled to the head 316.

Pole 82 attaches the second target marker 64 to the head 316 of the surgical instrument 300. Changes in the pose of the second target marker 64 are, therefore, directly indicative of the changes in the pose of the drill bit 312 of the surgical instrument 300.

The plurality of adjustment motors 310 are coupled to the surgical instrument 300 through a plurality of motor couplers 311a, 311b, 311c, and 311d (shown in FIG. 11) (herein referred to collectively as 311). Each adjustment motor 310 can have a corresponding motor coupler 311. The plurality of adjustment motors 310 are operatively coupled to the controller 50.

As shown in FIG. 11, the surgical instrument 300 has a transverse axis 303 that is orthogonal to the longitudinal axis 301. Surgical instrument 300 includes a pivotable attachment that can attach the head 316 to the handle 306 such that the longitudinal axis 301 (i.e., roll axis) of the head 316 relative to the handle 306 is co-axial with the roll axis of the driveshaft 320. That is, the handle 306 and the cutting portion 302 of the surgical instrument 300 have a nearly coaxial relationship in contrast to the nearly perpendicular relationship between the handle 106 and the cutting portion 102 of the handpiece 100.

Figure 12:
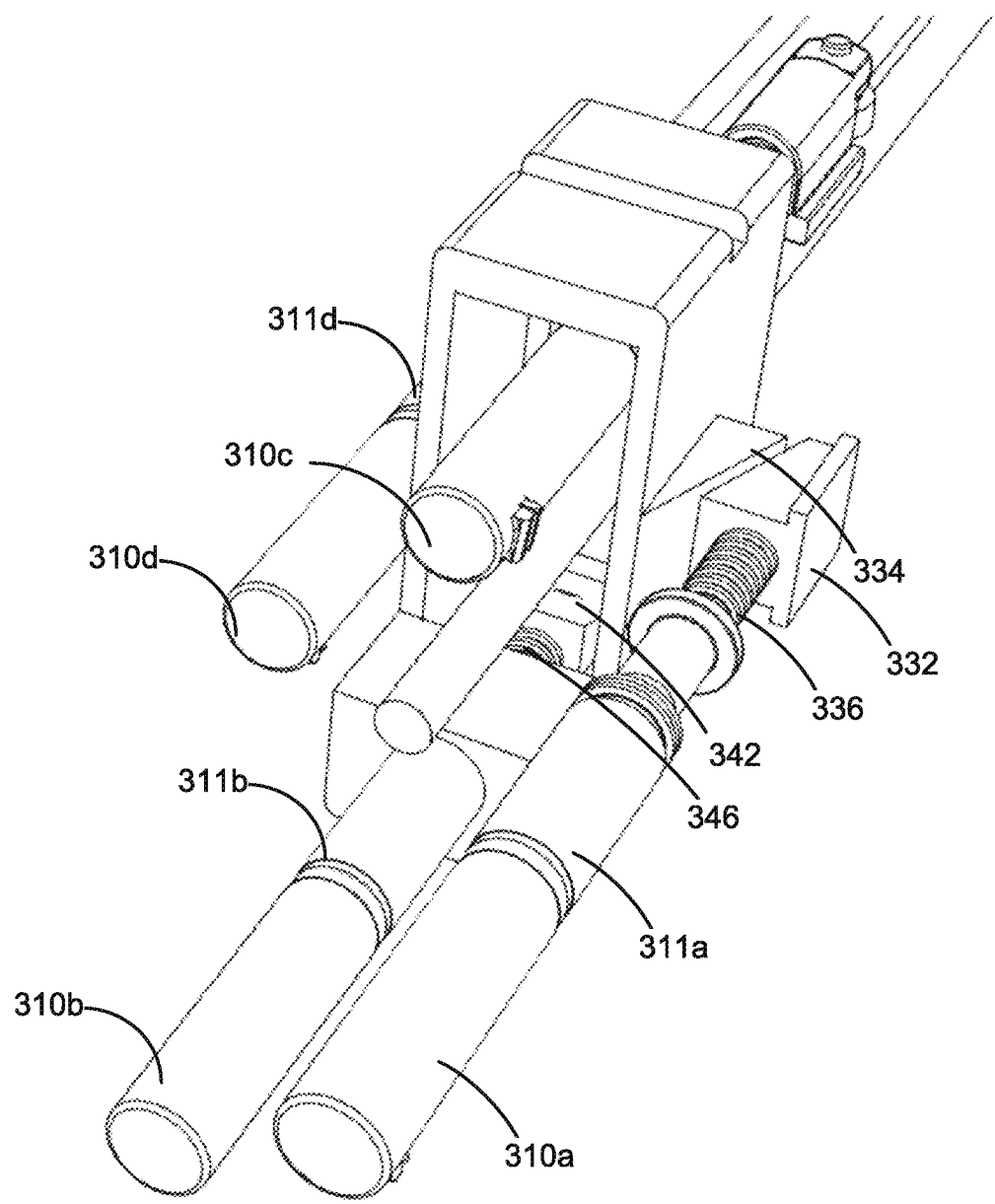
FIGS. 12 and 13 are example illustrations a translating mechanism of the floating assembly of the surgical instrument of FIG. 10, according to at least one embodiment.
Figure 13:
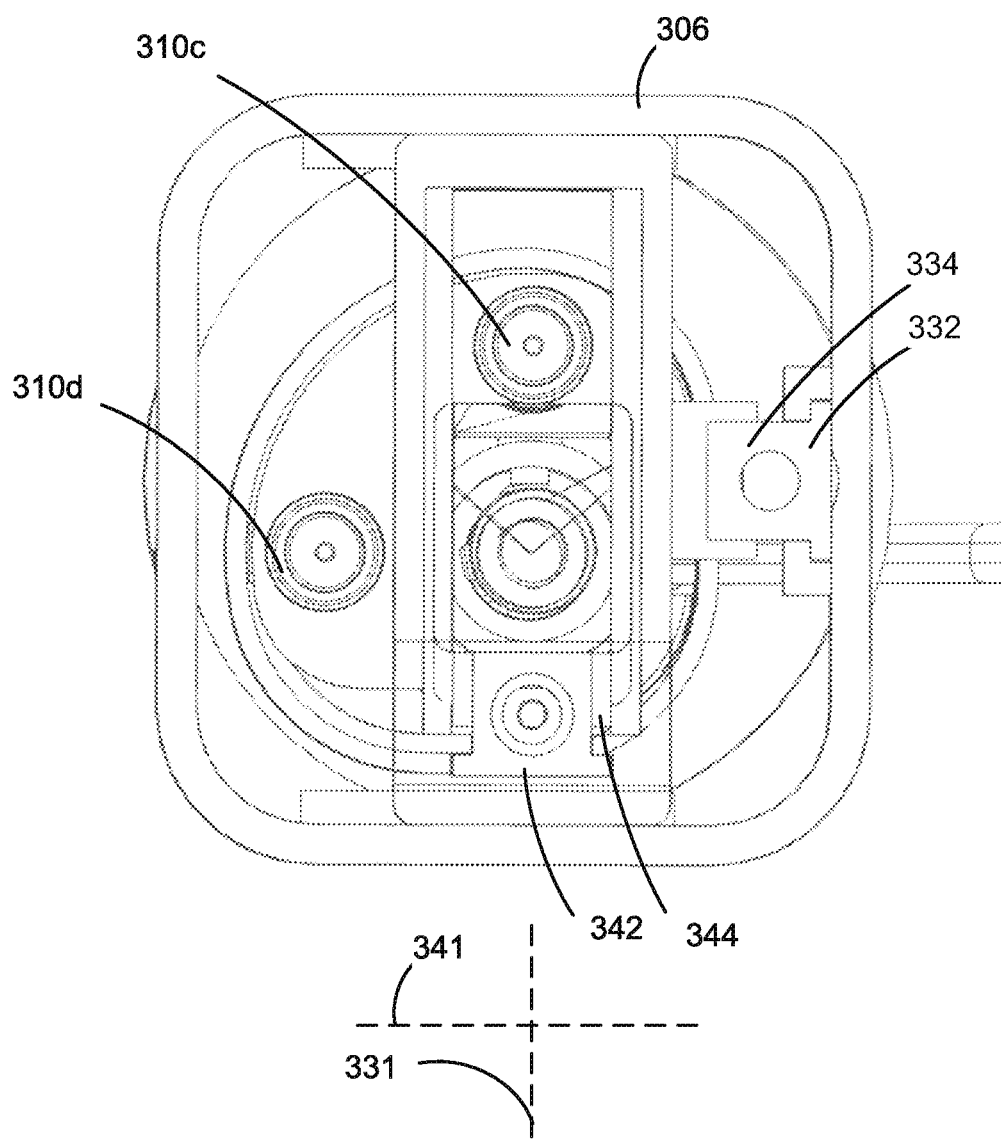

Referring now to FIGS. 12 and 13, shown therein are example illustrations of a translating mechanism for the floating assembly of the surgical instrument of FIG. 10, according to at least one embodiment. As set out above, the floating assembly 330 can move independently from the handle 306. For example, the floating assembly 330 can translate along a first axis 331 parallel to a transverse axis 303 of the surgical instrument 300 and translate along a second axis 341 perpendicular to the longitudinal axis 301.

Translation of the floating assembly 330 can translate the cutting portion 302. As shown in FIG. 12, a wedge system can be used to control translation in a first direction along the first axis 331 parallel to the transverse axis 303. For example, the adjustment motor 310a can be coupled to a first pan screw 336 through a motor coupler 311a for adjustment motor 310a. The first pan screw 336 can be further coupled to a first pan wedge 332. The first pan wedge 332 can be further coupled to a first pan ramp 334.

During operation, the adjustment motor 310a can actuate the first pan screw 336, causing the first pan screw 336 to rotate. Rotating the first pan screw 336 can cause the first pan wedge 332 to translate along the longitudinal axis 301. Translating the first pan wedge 332 forward along the longitudinal axis 301 (towards the drill bit 312) can cause the first pan wedge 332 to push against the first pan ramp 334 inwards. Pushing the first pan ramp 334 inwards causes the floating assembly 330 to move in the first direction along the first axis 331 parallel to the transverse axis 303. When the adjustment motor 310a translates the first pan wedge 332 rearward, the force against the first pan ramp 334 is reduced, and the floating assembly 330 can move in a second direction that is opposite to the first direction, along the first axis 331.

Similarly, a wedge system can be used to control translation along a second axis 341 perpendicular to both the first axis 331 and the longitudinal axis 301. For example, a second adjustment motor 310b can be coupled to a second pan screw 346 through a second motor coupler 311b for the second adjustment motor 310b. The second pan screw 346 can be further coupled to a second pan wedge 342. The second pan wedge 342 can be further coupled to a second pan ramp (not shown in FIGS. 12 and 13).

During operation, the second adjustment motor 310b can actuate the second pan screw, causing the second pan screw 346 to rotate. Rotating the second pan screw can 346 cause the second pan wedge 342 to translate along the longitudinal axis 301. Translating the second pan wedge 342 forward along the longitudinal axis 301 (towards the drill bit 312) can cause the second pan wedge 342 to push against the second pan ramp inwards. Pushing the second pan ramp inwards causes the floating assembly 330 to move in a first direction along the second axis 341. When the second adjustment motor 310b translates the second pan wedge 342 rearward, the force against the second pan ramp 344 is reduced, and the floating assembly 330 can move opposite the second direction that is opposite to the first direction, along the second axis 341.

Figure 14:
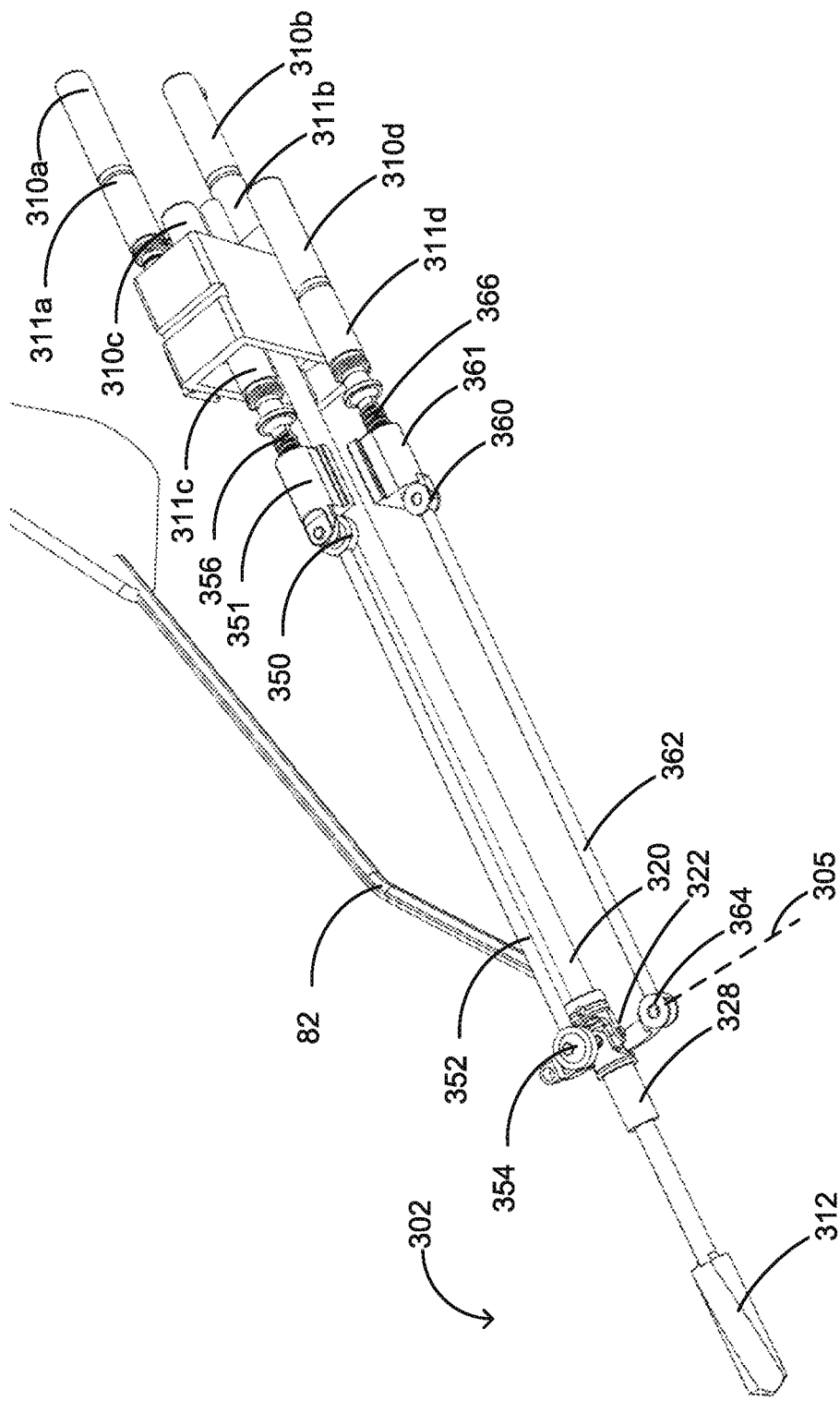
FIGS. 14 and 15 are example illustrations of a mechanism for controlling the tilt and yaw motions of the cutting portion of the surgical instrument of FIG. 10, according to at least one embodiment.
Figure 15:
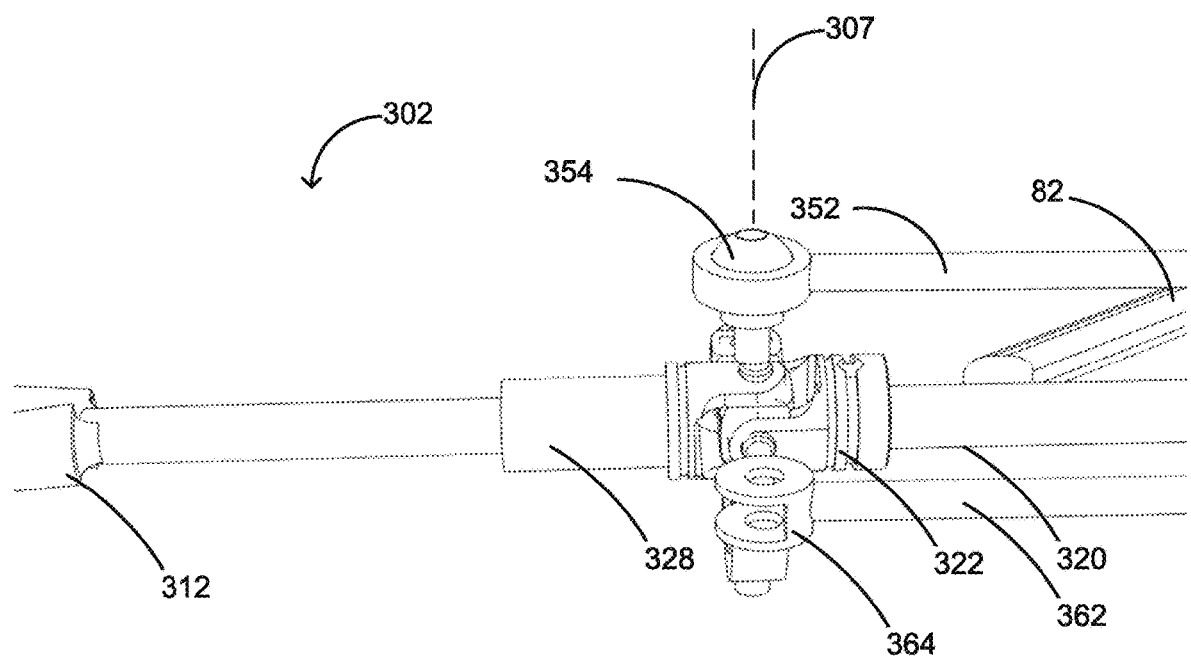

Referring now to FIGS. 14 and 15, shown therein are example illustrations of a mechanism for controlling the tilt and yaw motions of the cutting portion of the surgical instrument of FIG. 10, according to at least one embodiment. The adjustment motors 310 can control the tilt and yaw of the cutting portion 302.

The tilt of the cutting portion 302 can be controlled by the adjustment motor 310c. The adjustment motor 310c can be coupled to a tilt screw 356 though a motor coupler 311c for adjustment motor 310c. The tilt screw 356 can be further coupled to a tilt slider 351. The tilt slider 351 can be further coupled to a first tilt joint 350. The first tilt joint 350 can be further coupled to a tilt link 352. The tilt link 352 can be further coupled to a second tilt joint 354. The second tilt joint 354 can be further coupled to the cutting portion 302. In at least one embodiment, the first tilt joint 350, the second tilt joint 354, or both the first and second tilt joints 350, 354 can be spherical joints.

During operation, the adjustment motor 310c can actuate the tilt screw 356 through the motor coupler 311c for adjustment motor 310c. Actuating the tilt screw 356 can cause the tilt screw 356 to rotate in a first direction around axis 307 (shown in FIG. 15). Rotating the tilt screw 356 in the first direction can cause the tilt slider 351 to translate forward. Translating the tilt slider 351 forward can cause the first tilt joint 350 to translate tilt link 352 forward (toward the cutting portion 302). Causing the tilt link 352 to translate forward can cause the second tilt joint 354 to tilt the head 316 (not shown in FIGS. 14 and 15) in a first tilt direction. Similarly, when the adjustment motor 310c rotates the tilt screw 356 in a second direction around axis 307, the head 316 (not shown in FIGS. 14 and 15) can tilt in a second tilt direction.

The yaw motion of the cutting portion 302 can be controlled by the adjustment motor 310d. The adjustment motor 310d can be coupled to a yaw screw 366 through a motor coupler 311d for adjustment motor 310d. The yaw screw 366 can be further coupled to a yaw slider 361. The yaw slider 361 can be further coupled to a first yaw joint 360. The first yaw joint 360 can be further coupled to a yaw link 362. The yaw link 362 can be further coupled to a second yaw joint 364. The second yaw joint 364 can be further coupled to the head 316 (not shown in FIGS. 14 and 15). In some embodiments, the first and second yaw joints 360 and 364 can be cylindrical joints.

During operation, the adjustment motor 310d can actuate the yaw screw 366 through the motor coupler 311d. Actuating the yaw screw 366 can cause the yaw screw 366 to rotate in a first direction around axis 305 (shown in FIG. 14). Rotating the yaw screw 366 in a first direction can cause the yaw slider 361 to translate forward. Translating the yaw slider 361 forward can cause the first yaw joint 360 to translate the yaw link 362 forward (toward the cutting portion 302). Causing the yaw link 362 to translate forward can cause the second yaw joint 364 to yaw the head 316 (not shown in FIGS. 14 and 15) in a first yaw direction. Similarly, when the adjustment motor 310d rotates the yaw screw 366 in a second direction around axis 305 (shown in FIG. 14), the head 316 (not shown in FIGS. 14 and 15) can yaw in a second yaw direction.

As shown in FIG. 15, the driveshaft 320 can have a drive joint 322. The drive joint 322 can be coupled to a drill chuck 328, which is further coupled to the drill bit 312. During operation, the drive motor 308 can transmit torque to the drill bit 312 by actuating the driveshaft 320 and causing it to rotate. In turn, rotating the driveshaft 320 can cause the drill chuck 328, and therefore the drill bit 312, to rotate. In some embodiments, the drive joint 322 may be a Cardan joint.

In at least one embodiment, the cutting region 302 may be a cutting plane. In such embodiments, the cutting portion may be a saw. The saw may be driven using piezoelectric mechanisms. In such embodiments, the drive motor 308 is not necessary and can be replaced with an additional adjustment motor. The additional adjustment motor may roll the saw around a shaft, similar to how the drill bit 312 is rolled around its axis using the drill chuck 328. The controller 50 can then control the roll motion of the saw to align the cutting plane with a desired cutting plane in the planned cutting region 32.

In at least one embodiment, the user can selectively activate one or more of the plurality of degrees of freedom by disabling one or more of the plurality of adjustment motors 110, 210, 310. Even control over one or two degrees of freedom can reduce deviations between the cutting pose and the desired pose. For example, the surgical instrument 100, 200, 300 can have computer-controlled adjustment of only the tilt, yaw, or roll angles, but not the pan position. Computer-controlled adjustment of the angular degrees of freedom can reduce the difficulty of the surgery for the user. Furthermore, having computer-controlled adjustment of fewer degrees of freedom may be preferred in cases where cost, weight, reliability, and ease of maintenance are paramount considerations. In such cases, the mechanisms related to the degrees of freedom that are not computer-controlled may simply be removed from the design.

In at least one embodiment, the surgical instrument 100, 200, 300 can measure cutting criteria during the surgery. For example, the surgical instrument 100, 200, 300 can measure a cutting resistance in the surgical subject 30. The surgical instrument 100, 200, 300 can measure an electrical impedance of the surgical subject 30. For example, the surgical instrument 100, 200, 300 can have a sensor that measures the amount of force the user exerts on the surgical instrument 100, 200, 300 to drill into the surgical subject 30. When too much force is exerted on the surgical instrument 100, 200, 300, the cutting portion 102, 202, 302 can descend into the surgical subject 30 too rapidly and injure the patient, particularly if the bone density of the surgical subject 30 is low. Controller 50 can then issue a warning to the user to take greater care in their surgery to ensure that the patient is not injured and that the desired path 32 is followed. In another embodiment, the controller 50 can automatically operate the adjustment motors 110, 210, 310 to reduce the speed of the cutting and/or to reduce the torque generated by drive motor 208, 308 to slow down the cutting rate.

Figure 16:
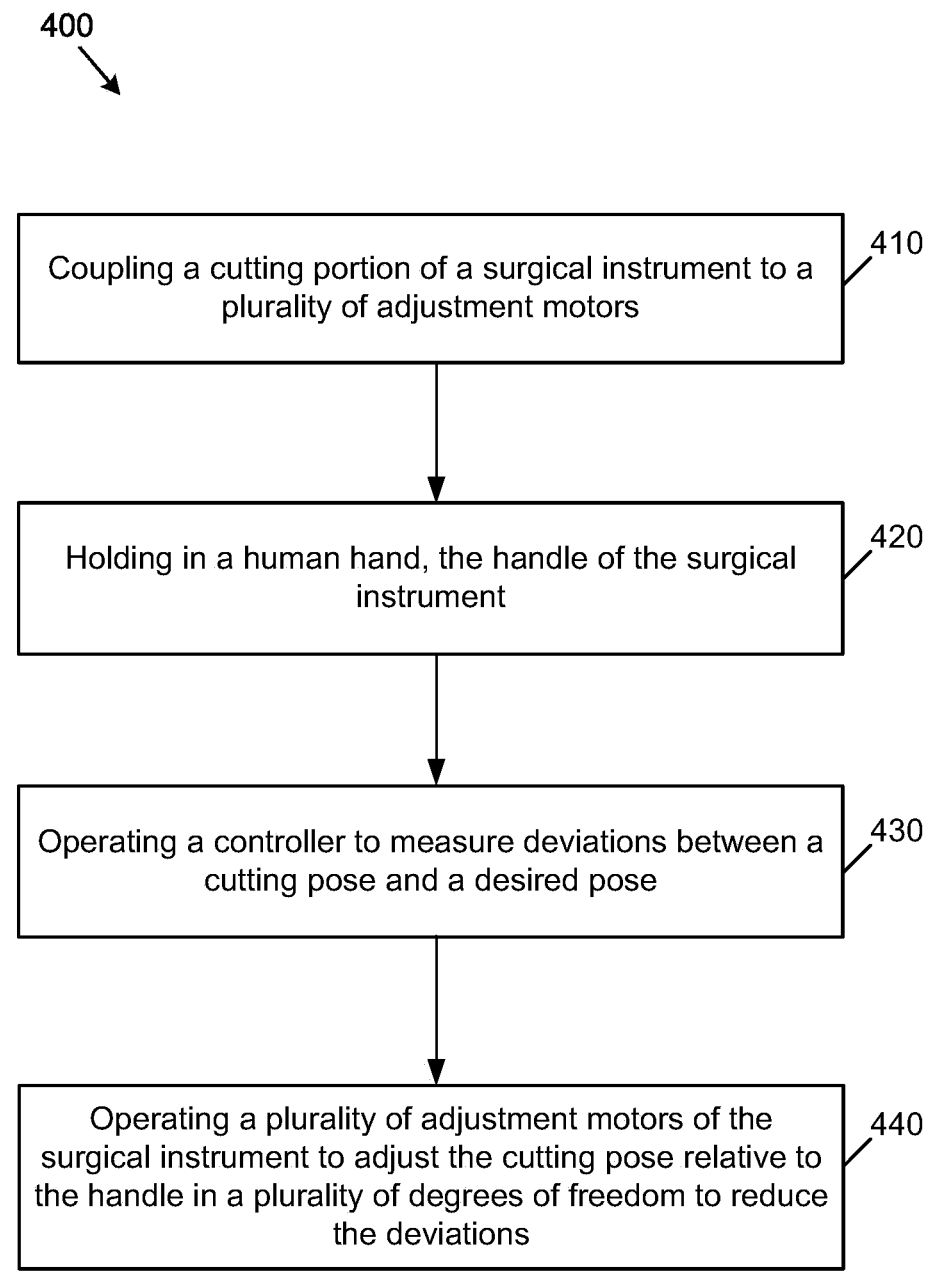
FIG. 16 is flowchart of an example method of controlling a surgical instrument, according to at least one embodiment.

Referring now to FIG. 16, shown therein is an example method 400 of controlling a surgical instrument, according to at least one embodiment. The surgical instrument can be, for example surgical instrument 100, 200, or 300.

Method 400 can begin at act 410, in which a cutting portion of a surgical instrument is coupled to a plurality of adjustment motors. At act 420, the surgical instrument is held by a user. In particular, the user holds a handle of the surgical instrument. The handle can be, for example, handle 106, 206, or 306 of surgical instruments 100, 200, or 300, respectively.

At act 430, a computerized controller is operated to measure deviations between a cutting pose of the cutting portion and a desired pose of the cutting portion. The computerized controller can be, for example, controller 50 of system 10. Act 430 can include storing in a computer-readable memory in electronic communication with the computerized controller, a geometrical descriptor of a cutting path or region within an anatomical region being operated on. The anatomical region can be, for example, a patient's jaw 34. Act 430 can include operating the computerized controller to determine the desired pose from the geometrical descriptor. Act 430 can include using a pose tracking system with the computerized controller. The pose tracking system can be, for example pose tracking system 60. Measuring deviations between the cutting pose and the desired pose of the cutting portion can involve tracking the cutting pose relative to the anatomical region.

Act 430 may include defining the geometrical descriptor relative to an image of the anatomical region. Measuring deviations between the cutting pose and the desired pose of the cutting portion can involve operating the computerized controller to compute a registration mapping between the image and the anatomical region, and then using that registration mapping to determine the deviations.

At act 440, a plurality of adjustment motors of the surgical instrument are operated to adjust the cutting pose relative to the handle in a plurality of degrees of freedom to reduce the deviations. The plurality of adjustment motors can be, for example adjustment motors 210, 310 of the surgical instruments 200, 300, respectively.

In at least one embodiment, after completing the use of the surgical instrument involving operating the plurality of adjustment motors to adjust the cutting pose relative to the handle, the method 400 can also involve detaching the adjustment motors from the surgical instrument and the cutting portion thereof. In addition, the surgical instrument can be sterilized without the adjustment motors but including the cutting portion. Furthermore, the adjustment motors can be reattached to the surgical instrument and the cutting portion thereof.

Various embodiments have been described herein by way of example only. Various modification and variations may be made to these example embodiments without departing from the spirit and scope of the invention, which is limited only by the appended claims.

The invention claimed is:

1. A surgical system comprising:
a surgical instrument having a cutting portion and a body, the body having a handle, a drive motor for driving the cutting portion in a rotating, a reciprocating or a vibrating motion, a plurality of adjustment motors for adjusting a cutting pose of the cutting portion relative to the handle in a plurality of degrees of freedom; and,
a controller configured to measure the deviations between the cutting pose of the cutting portion and a desired pose of the cutting portion in the plurality of degrees of freedom and to then activate the adjustment motors to reduce those deviations,
wherein the drive motor has a drive motor axis and the cutting portion is adjustably angled relative to the drive motor axis such that an angle of the cutting portion relative to the drive motor axis is adjustable by at least one of the plurality of adjustment motors.

2. The surgical system as defined in claim 1, wherein the plurality of adjustment motors are connected to the cutting portion to, in operation, adjust the pose of the cutting portion to reduce the deviations while a force of 5 Newtons (N) is applied to the cutting portion in a direction opposing the adjustment.

3. The surgical system as defined in claim 1, wherein the controller further comprises:
a pose tracking system for tracking a pose of the cutting portion of the instrument relative to the anatomical region being operated on;
a computer-readable memory for storing a geometrical descriptor of a cutting path or region within the anatomical region; and
a processor in electronic communication with the computer-readable memory and the pose tracking system, configured to determine the deviations based on the pose reported by the pose tracking system and the desired pose determined from the geometrical descriptor.

4. The surgical system as defined in claim 3, wherein: the pose tracking system further comprises:
a first marker configured to be attached to the anatomical region;
a second marker attached to a part of the body of the surgical instrument;
a sensor for measuring a value indicative of the spatial relationship between the cutting portion and the part of the body of the surgical instrument to which the second marker is attached; and
the pose tracking system is further operable to measure the spatial relationship between the first and second markers; and
the processor is configured to compute the cutting pose of the cutting portion relative to the anatomical region based on the measurements obtained from the pose tracking system and the sensor.

5. The surgical system as defined in claim 4, wherein the distance from the cutting portion to the second marker attached to a part of the body of the surgical instrument is at least 5 centimeters (cm).

6. The surgical system as defined in claim 3, wherein:
the geometrical descriptor comprises a linear drilling path;
the cutting portion comprises a drill bit rotatable around a drilling axis;
the drive motor drives the drill bit in the rotating motion about the drilling axis; and,
the deviations comprise two angles of difference in orientation between the drilling axis and the drilling path.

7. The surgical system as defined in claim 3, wherein:
the geometrical descriptor comprises a linear drilling path;
the cutting portion comprises a drill bit rotating around a drilling axis;
the drive motor drives the drill bit in the rotating motion about the drilling axis; and,
the deviations comprise a 2-dimensional translation vector describing the difference between a location on the drilling axis and a location on the drilling path.

8. The surgical system as defined in claim 3, wherein:
the geometrical descriptor is defined relative to an image of the anatomical region; and
the processor is further configured to compute a registration mapping between the image and the anatomical region, and to use that registration mapping in determining the deviations.

9. The surgical system as defined in claim 3, wherein:
the cutting region is a cutting path; and
the cutting portion is a saw.

10. The surgical system as defined in claim 3, wherein:
the cutting region is a 3D volume to be removed from the anatomical region; and
the cutting portion is a burr.

11. The surgical system as defined in claim 1, wherein:
the surgical instrument further comprises a head, and a pivotable attachment attaching the head to the body, the head comprising the cutting portion;
the surgical instrument further comprises a driveshaft for transmitting torque from the drive motor to the cutting portion within a contact region;
the head comprises a cutting portion contact surface located within the contact region, the cutting portion contact surface being coupled to the cutting portion to drive the cutting portion;
the body comprises a torque transmission surface located within the contact region, the torque transmission surface being coupled to the driveshaft to be driven by the driveshaft, the torque transmission surface contacting the cutting portion contact surface to transfer torque thereto; and the cutting portion contact surface and the torque transmission surface remain in contact through a range of adjustments in the plurality of degrees of freedom to transmit torque from the drive motor to the cutting portion.

12. The surgical system as defined in claim 11, wherein: the plurality of adjustment motors comprise a head translation motor configured to rotate the head relative to the handle around an axis substantially perpendicular to both the roll axis and a lateral adjustment direction.

13. The surgical system as defined in claim 1, wherein: the surgical instrument further comprises a driveshaft for transmitting torque from the drive motor to the cutting portion; and
the surgical instrument further comprises a head comprising the cutting portion, and a pivotable attachment attaching the head to the handle such that the roll axis of the head relative to the handle is co-axial with the roll axis of the driveshaft.

14. The surgical system as defined in claim 1, further comprising a display indicating the deviations between an imaginary pose of the cutting portion when each adjustment motor is set to approximately a middle 20% of its operating range and the desired pose of the cutting portion.

15. The surgical system as defined in claim 1, wherein the adjustment motors are detachable from the parts of the instrument comprising the handle and the cutting portion such that the handle and the cutting portion are steam sterilizable without sterilizing the adjustment motors when the adjustment motors are detached.

16. The surgical system as defined in claim 1, further comprising a driveshaft housing positioned within the handle, wherein the driveshaft housing is rotatable relative to the handle.

17. A method of controlling a surgical instrument, the method comprising:
coupling a cutting portion of a surgical instrument to a plurality of adjustment motors;
holding in a human hand, a handle of the surgical instrument;
operating a computerized controller to measure deviations between a cutting pose of the cutting portion and a desired pose of the cutting portion;
driving the cutting portion with a drive, the drive having a drive axis, and
operating the plurality of adjustment motors to adjust the cutting pose relative to the handle in a plurality of degrees of freedom to reduce the deviations by operating at least one of the plurality of adjustment motors to adjust an angle of the cutting pose relative to the drive axis to reduce the deviations.

18. The method as defined in claim 17 further comprising:
storing in a computer-readable memory in electronic communication with the computerized controller, a geometrical descriptor of a cutting path or region within an anatomical region being operated on; and
operating the computerized controller to determine the desired pose from the geometrical descriptor;
wherein,
the computerized controller comprises a pose tracking system; and
operating the computerized controller to measure deviations between the cutting pose and the desired pose of the cutting portion comprises tracking the cutting pose relative to the anatomical region.

19. The method as defined in claim 18 further comprising:
defining the geometrical descriptor relative to an image of the anatomical region; and,
operating the computerized controller to measure deviations between the cutting pose and the desired pose of the cutting portion comprises operating the computerized controller to compute a registration mapping between the image and the anatomical region, and then using that registration mapping to determine the deviations.

20. The method as defined in claim 17 further comprising, after completing a use of the surgical instrument involving operating the plurality of adjustment motors to adjust the cutting pose relative to the handle,
detaching the adjustment motors from the surgical instrument and the cutting portion thereof;
sterilizing the surgical instrument without the adjustment motors but including the cutting portion; and then
reattaching the adjustment motors to the surgical instrument and the cutting portion thereof.

21. The method as defined in claim 17, further comprising driving the cutting portion with the drive while at least one of the plurality of adjustment motors adjusts the angle of the cutting pose.

* * * * *